United States Patent [19]

Uekawa et al.

[11] Patent Number: 5,354,729
[45] Date of Patent: Oct. 11, 1994

[54] N-ACYLDIHYDROQUINOLINE DERIVATIVES, A METHOD FOR PRODUCING THE SAME AND THEIR USE AS HERBICIDES

[75] Inventors: Toru Uekawa, Takarazuka; Mitsunori Hiratsuka, Toyonaka; Naonori Hirata, Sanda; Kazuo Saito, Toyonaka; Hiroyuki Yogai, Kobe, all of Japan

[73] Assignee: Sumitomo Chemical Company, Limited, Osaka, Japan

[21] Appl. No.: 89,576

[22] Filed: Jul. 12, 1993

[30] Foreign Application Priority Data

Jul. 15, 1992 [JP] Japan .................. 4-188043

[51] Int. Cl.$^5$ .................. A01N 43/48; C07D 401/02; C07D 215/12
[52] U.S. Cl. .................. 504/235; 504/247; 544/405; 546/168
[58] Field of Search .................. 544/405; 546/168; 504/235, 247

[56] References Cited

FOREIGN PATENT DOCUMENTS 461079 12/1991 European Pat. Off. .
1068487 4/1986 Japan .
09577 6/1992 PCT Int'l Appl. .

OTHER PUBLICATIONS

*J. Pesticide Sci.*, vol. 13, pp. 71–75 (1988), Tadashi Ohsumi et al., "Herbicidal Activity of Carbamoylimidazoles with Steric Hindrance".

*Primary Examiner*—Cecilia Tsang
*Attorney, Agent, or Firm*—Stevens, Davis, Miller & Mosher

[57] ABSTRACT

The present invention relates to novel N-acyldihydroquinoline derivatives, a method for producing the same and their use as herbicides.

12 Claims, No Drawings

N-ACYLDIHYDROQUINOLINE DERIVATIVES, A METHOD FOR PRODUCING THE SAME AND THEIR USE AS HERBICIDES

The present invention relates to novel N-acyldihydroquinoline derivatives, a method for producing the same and their use as herbicides.

It is well known in the art that certain kinds of compounds can be used as active ingredients for herbicides.

However, these compounds are not always said to be satisfactory because they are insufficient as herbicides.

In view of these circumstances, the present inventors have extensively studied, and as a result, have found that N-acyldihydroquinoline derivatives represented by the following formula (I) are excellent compounds as herbicides which can control weeds widely generated in crop lands or non-crop lands at low dosage rate, have a broad herbicidal spectrum and also can safely be used for no-till cultivation. The present invention is based on this finding.

The present invention provides N-acyldihydroquinoline derivatives represented by the formula (I) [hereinafter referred to as the present compound(s)], a method for producing the same and their use as herbicides:

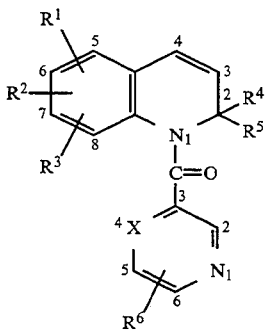

wherein each of $R^1$, $R^2$ and $R^3$, which may be the same or different, represents a hydrogen atom; a halogen atom; a $C_1$–$C_6$ alkyl group; a $C_1$–$C_6$ alkoxy group; a halo-$C_1$–$C_6$ alkyl group; a halo-$C_1$–$C_6$ alkoxy group; a ($C_1$–$C_6$ alkoxy)carbonyl group; a $C_1$–$C_6$ alkylthio group; a $C_1$–$C_6$ alkylamino group; a di($C_1$–$C_6$ alkyl)amino group; a phenyl group; or a phenoxy group, each of $R^4$ and $R^5$, which may be the same or different, represents a hydrogen atom or a $C_1$–$C_6$ alkyl group, or $R^4$ and $R^5$ are bonded together at their ends to form a $C_2$–$C_5$ alkylene group, $R^6$ represents a hydrogen atom; a halogen atom; an amino group; a $C_1$–$C_6$ alkylamino group; a di($C_1$–$C_6$ alkyl)amino group; a ($C_1$–$C_6$ alkoxy)carbonylamino group; a cyano group; or a group represented by the formula, —C(=O)—Y—$R^7$ (wherein Y represents an oxygen atom or a sulfur atom and $R^7$ represents a hydrogen atom; a $C_1$–$C_{10}$ alkyl group; a $C_2$–$C_{10}$ alkenyl group; a $C_2$–$C_{10}$ alkynyl group; a halo-$C_1$–$C_{10}$ alkyl group; a halo-$C_2$–$C_{10}$ alkenyl group; a halo-$C_2$–$C_{10}$ alkynyl group; a $C_3$–$C_{10}$ cycloalkyl group; a $C_3$–$C_{10}$ cycloalkenyl group; a $C_1$–$C_{10}$ alkoxy-$C_1$–$C_{10}$ alkyl group; a $C_1$–$C_{10}$ alkylamino-$C_1$–$C_{10}$ alkyl group; a di($C_1$–$C_{10}$ alkyl)amino-$C_1$–$C_{10}$ alkyl group; a furyl-$C_1$–$C_{10}$ alkyl group; a thienyl-$C_1$–$C_{10}$ alkyl group; a $C_1$–$C_1$-aikylamino group; a di($C_1$–$C_{10}$ alkyl) amino group;

—N=CH($C_1$–$C_{10}$ alkyl) group;

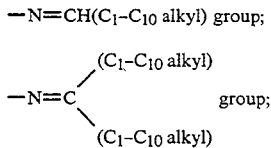

or a phenyl group optionally substituted with at least one member selected from the group consisting of ($C_1$–$C_6$ alkoxy)carbonyl groups, halogen atoms and $C_1$–$C_6$ alkyl groups; or a phenyl-$C_1$–$C_6$ alkyl group optionally substituted with at least one member selected from the group consisting of ($C_1$–$C_6$ alkoxy)carbonyl groups, halogen atoms and $C_1$–$C_6$ alkyl groups); or a group of the formula,

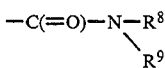

(wherein each of $R^8$ and $R^9$, which may be the same or different, represents a hydrogen atom; a $C_1$–$C_6$ alkyl group; a $C_2$–$C_6$ alkenyl group; a $C_2$–$C_6$ alkynyl group; a halo-$C_1$–$C_6$ alkyl group; a halo-$C_2$–$C_6$ alkenyl group; a halo-$C_2$–$C_6$ alkynyl group; a $C_3$–$C_6$ cycloalkyl group; a $C_3$–$C_6$ cycloalkenyl group; an amino group; a $C_1$–$C_6$ alkylamino group; a di($C_1$–$C_6$ alkyl)amino group; or a phenyl group optionally substituted with at least one member selected from the group consisting of halogen atoms and $C_1$–$C_6$ alkyl groups; or a phenyl-$C_1$–$C_6$ alkyl group optionally substituted with at least one member selected from the group consisting of halogen atoms and $C_1$–$C_6$ alkyl groups, X represents CH or a nitrogen atom.

The number of carbon is preferably 1–3 in substituents $R^1$, $R^2$, $R^3$, $R^4$, $R^5$ and $R^6$ and 1–6 in substituent $R^7$, $R^8$ and $R^9$.

More specifically, it is preferable that each of $R^1$, $R^2$ and $R^3$, which may be the same or different, represents a hydrogen atom; a halogen atom; a $C_1$–$C_3$ alkyl group; a $C_1$–$C_3$ alkoxy group; a halo-$C_1$–$C_3$ alkyl group; a halo-$C_1$–$C_3$ alkoxy group; a ($C_1$–$C_3$ alkoxy)carbonyl group; a $C_1$–$C_3$ alkylthio group; a $C_1$–$C_3$ alkylamino group; a di($C_1$–$C_3$ alkyl)amino group; a phenyl group; or a phenoxy group, each of $R^4$ and $R^5$, which may be the same or different, represents a hydrogen atom or a $C_1$–$C_3$ alkyl group, or $R^4$ and $R^5$ are bonded together at their ends to form a $C_2$–$C_3$ alkylene group, $R^6$ represents a hydrogen atom; a halogen atom; an amino group; a $C_1$–$C_3$ alkylamino group; a di($C_1$–$C_3$ alkyl)amino group; a ($C_1$–$C_3$ alkoxy)carbonylamino group; a cyano group; or a group represented by the formula, —C(=O)—Y—$R^7$ (wherein Y represents an oxygen atom or a sulfur atom and $R^7$ represents a hydrogen atom; a $C_1$–$C_6$ alkyl group; a $C_2$–$C_6$ alkenyl group; a $C_2$–$C_6$ alkynyl group; a halo-$C_1$–$C_6$ alkyl group; a halo-$C_2$–$C_6$ alkenyl group; a halo-$C_2$–$C_6$ alkynyl group; a $C_3$–$C_6$ cycloalkyl group; a $C_3$–$C_6$ cycloalkenyl group; a $C_1$–$C_6$ alkoxy-$C_1$–$C_6$ alkyl group; a $C_1$–$C_6$ alkylamino-$C_1$–$C_6$ alkyl group; a di($C_1$–$C_6$ alkyl)amino-$C_1$–$C_6$ alkyl group; a furyl-$C_1$–$C_6$ alkyl group; a thienyl-$C_1$–$C_6$ alkyl group; a $C_1$–$C_6$ alkylamino group; a di($C_1$–$C_6$ alkyl)amino group;

—N=CH($C_1$–$C_6$ alkyl) group;

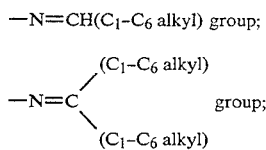
group;

or a phenyl group optionally substituted with at least one member selected from the group consisting of ($C_1$–$C_6$ alkoxy)carbonyl groups, halogen atoms and $C_1$–$C_6$ alkyl groups; or a phenyl-$C_1$–$C_6$ alkyl group optionally substituted with at least one member selected from the group consisting of ($C_1$–$C_6$ alkoxy)carbonyl groups, halogen atoms and $C_1$–$C_6$ alkyl groups); or a group represented by the formula

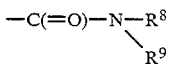

(wherein each of $R^8$ and $R^9$, which may be the same or different, represents a hydrogen atom; a $C_1$–$C_6$ alkyl group; a $C_2$–$C_6$ alkenyl group; a $C_2$–$C_6$ alkynyl group; a halo-$C_1$–$C_6$ alkyl group; a halo-$C_2$–$C_6$ alkenyl group; a halo-$C_2$–$C_6$ alkynyl group; a $C_3$–$C_6$ cycloalkyl group; a $C_3$–$C_6$ cycloalkenyl group; an amino group; a $C_1$–$C_6$ alkylamino group; a di($C_1$–$C_6$ alkyl)amino group; or a phenyl group optionally substituted with at least one member selected from the group consisting of halogen atoms and $C_1$–$C_6$ alkyl groups; or a phenyl-$C_1$–$C_6$ alkyl group optionally substituted with at least one member selected from the group consisting of halogen atoms and $C_1$–$C_6$ alkyl groups).

In the compound of the formula (I), each of $R^4$ and $R^5$, which may be the same or different, is preferably a $C_1$–$C_3$ alkyl group, and more preferably both of $R^4$ and $R^5$ are methyl groups.

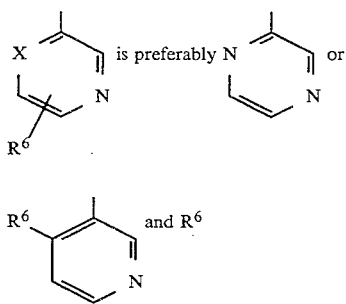

is preferably a hydrogen atom, a halogen atom, a cyano group, or a group represented by the formula, —C(=O)—Y—$R^7$, or a group represented by the formula,

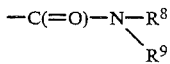

and more preferably a group represented by the formula, —C(=O)—Y—$R^7$ or a group represented by the formula,

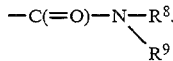

$R^1$ is preferably at 6-position and $R^1$ is preferably a halogen atom, a $C_1$–$C_3$ alkyl group or a phenyl group, and more preferably a halogen atom and each of $R^2$ and $R^3$ is preferably a hydrogen atom.

In $R^1$, $R^2$, $R^3$, $R^4$, $R^5$, $R^6$, $R^8$ and $R^9$, examples of alkyl groups and alkyl moiety of alkylthio, alkylamino, dialkylamino and phenylalkyl groups include methyl, ethyl, n-propyl, i-propyl, n-butyl, sec-butyl, tert-butyl, n-hexyl groups and the like;

examples of alkoxy groups and alkoxy moiety of haloalkoxy, alkoxycarbonyl and alkoxycarbonylamino groups include methoxy, ethoxy, n-propoxy, i-propoxy, n-butoxy, n-hexyloxy groups and the like;

examples of alkenyl groups and alkenyl moiety of haloalkenyl groups include vinyl, allyl, 1-butenyl, 2-butenyl, 3-butenyl, 2-pentenyl, 3-pentenyl, 2-hexenyl groups and the like;

examples of alkynyl groups and alkynyl moiety of haloalkynyl include ethynyl, propargyl, 1-butynyl, 2-butynyl, 2-pentynyl, 3-pentynyl, 2-hexynyl groups and the like;

examples of cycloalkyl groups include cyclopropyl, cyclobutyl, cyclopentyl, cyclohexyl groups and the like;

examples of cycloalkenyl groups include cyclopropenyl, 1-cyclobutenyl, 2-cyclobutenyl, 1-cyclopentenyl, 3-cyclopentenyl, 1-cyclohexenyl groups and the like;

examples of a halogen atom and halogen moiety of haloalkyl, haloalkenyl, haloalkynyl, haloalkoxy groups include fluorine, chlorine and bromine;

examples of haloalkyl groups include 2-chloroethyl, 2-bromoethyl, 3-fluoropropyl, 2-chloropropyl, 4-chlorobutyl, 6-chlorohexyl groups and the like;

examples of haloalkoxy groups include fluoromethoxy, dibromomethoxy, trifluoromethoxy, 1,1,2,2-tetrafluorohexyloxy, 1,1-dichloroethoxy, 1-chloro-2-bromobutoxy groups and the like;

examples of haloalkenyl groups include 1-chlorovinyl, 3-chloroallyl, 5-bromo-2-pentenyl, 6-fluoro-2-hexenyl, 5,5,5-trifluoro-2-pentenyl groups and the like;

examples of haloalkynyl groups include 2-chloroethynyl, 5-bromo-2-pentynyl, 6-fluoro-2-hexynyl, 5,5,5-trifluoro-2-pentynyl groups and the like;

examples of alkylamino groups include methylamino, ethylamino, n-propylamino, i-propylamino, n-butylamino, sec-butylamino, tert-butylamino, n-hexylamino groups and the like;

examples of dialkylamino groups include dimethylamino, methylethylamino, dipropylamino, methylhexylamino groups and the like;

examples of phenyl groups optionally substituted with at least one member selected from the group consisting of alkyl groups and halogen atoms include phenyl, 2-methylphenyl, 3-ethylphenyl, 4-hexylphenyl, 2,6-dimethylphenyl, 2-fluorophenyl, 2-chlorophenyl, 3-bromophenyl, 2,4-dichlorophenyl, 2-chloro-4-methylphenyl and the like; and examples of alkylene groups include ethylene, tetramethylene, pentamethylene and the like.

In $R^7$, examples of alkyl groups and alkyl moiety of haloalkyl, alkoxyalkyl, alkylaminoalkyl, di(alkylamino)alkyl, phenylalkyl, furylalkyl, thienylalkyl, alkylamino, dialkylamino, alkylimino and dialkylimino groups include, in addition to the examples mentioned above, heptyl, octyl, nonyl, decyl groups and the like;

examples of alkenyl groups and alkenyl moiety of haloalkenyl groups include, in addition to the examples mentioned above, heptenyl, octenyl, decenyl groups and the like;

examples of alkynyl groups and alkynyl moiety of haloalkynyl groups include, in addition to the examples mentioned above, heptynyl, octynyl, decynyl groups and the like;

examples of haloalkyl groups include, in addition to the examples mentioned above, 2-fluoroheptyl, 3-chlorooctyl, 2-bromodecyl groups and the like;

examples of haloalkenyl groups include in addition to the examples mentioned above, 3-chloro-2-heptenyl, 3-chloro-2-octenyl, 5-bromo-2-decenyl, 6-fluoro-2-heptenyl, 5,5,5-trichloro-2-heptenyl groups and the like;

examples of cycloalkyl groups include, in addition to the examples mentioned above, cycloheptyl, cyclooctyl, cyclodecyl groups and the like;

examples of cycloalkenyl groups include, in addition to the examples mentioned above, cycloheptenyl, cyclooctenyl, cyclodecenyl groups and the like;

examples of alkoxyalkyl groups include methoxymethyl, ethoxymethyl, 2-methoxyethyl, 3-ethoxypropyl, 4-n-propoxybutyl, 4-n-butoxyethyl, 6-hexyloxyhexyl, 2-ethoxyheptyl, 3-i-butoxydecyl, 4-n-decyloxybutyl groups and the like;

examples of alkylaminoalkyl groups include methylaminomethyl, ethylaminomethyl, butylaminomethyl, hexylaminoethyl, octylaminoethyl, methylaminopropyl, ethylaminohexyl, methylaminodecyl and the like;

examples of dialkylaminoalkyl groups include dimethylaminomethyl, diethylaminomethyl, methylbutylaminomethyl, methylhexylaminoethyl, dipropylaminobutyl, diethylaminohexyl, dimethylaminodecyl groups and the like;

examples of alkylamino groups include, in addition to the examples mentioned above, heptylamino, octylamino, decylamino groups and the like;

examples of dialkylamino groups include, in addition to the examples mentioned above, diheptylamino, methyloctylamino, ethyldecylamino groups and the like;

examples of —N=CH($C_1$-$C_{10}$ alkyl) group include —N=CHCH$_3$, —N=CHC$_2$H$_5$, —N=CHC$_3$H$_7$, -N=CHC$_6$H$_{13}$, —N=CHC$_{10}$H$_{21}$ and the like;

examples of —N=C$\begin{smallmatrix}(C_1-C_{10}\text{ alkyl})\\(C_1-C_{10}\text{ alkyl})\end{smallmatrix}$ group include —N=C(CH$_3$)$_2$, —N=C(CH$_3$)C$_2$H$_5$, —N=C(C$_3$H$_7$)$_2$, —N=C(CH$_3$)C$_6$H$_{13}$, —N=C(C$_7$H$_{15}$)$_2$, —N=C(CH$_3$)C$_{10}$H$_{21}$ and the like; and examples of phenyl groups or phenylalkyl groups, optionally substituted with at least one member selected from the group consisting of alkyl groups, halogen atoms and alkoxycarbonyl groups include, in addition to the examples mentioned above, 3-methoxycarbonylphenyl, 3-ethoxycarbonylphenyl, 4-i-propoxycarbonylphenyl, 3-hexyloxycarbonylphenyl, 2-phenylmethyl, phenylethyl, phenylhexyl, phenyldecyl, 2-methoxycarbonylphenylethyl, 2-ethoxycarbonylphenylbutyl, 2-n-propoxycarbonylphenylmethyl, 2-hexyloxycarbonylphenylhexyl, 2-methoxycarbonylphenyldecyl, 2-fluorophenylbutyl, 3-fluorophenylmethyl, 2-chlorophenylhexyl, 3-bromophenyldecyl, 2,4-dichlorophenylethyl, 2-methylphenylethyl, 3-ethylphenylhexyl, 4-hexylphenylbutyl, 2-methylphenyldecyl, 2,6-dimethylphenylethyl, 2-chloro-4-methylphenylethyl, 2-fluoro-4-methoxycarbonylphenylethyl groups and the like.

A method for producing the present compound is as follows:

The present compound (I) can be produced by reacting a dihydroquinoline derivative represented by the formula (II),

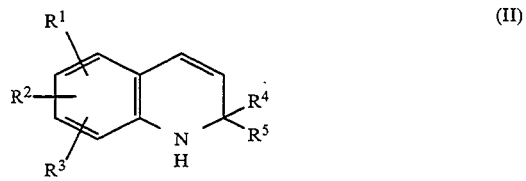

[wherein $R^1$, $R^2$, $R^3$, $R^4$ and $R^5$ are as defined above], with a compound represented by the formula (III),

wherein X and $R^6$ are each as defined above and $W^1$ represents a halogen atom].

This reaction is usually carried out with or without a solvent in the presence of a dehydrohalogenating agent. The reaction temperature usually ranges from room temperature to the boiling point of the solvent, and the reaction time ranges from 1 hour to 24 hours. Referring to the amounts of the reagents used for this reaction, the amount of the compound (III) is 1 to 3 equivalents based on 1 equivalent of the dihydroquinoline derivative (II), and that of the dehydrohalogenating agent is 1 to 5 equivalents based on the same. The solvent includes aliphatic hydrocarbons (e.g. hexane, heptane, ligroin, petroleum ether), aromatic hydrocarbons (e.g. benzene, toluene, xylene), halogenated hydrocabons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), water and mixtures thereof.

The dehydrohalogenating agent includes organic bases (e.g. pyridine, triethylamine, N,N-diethylaniline, 4-(N,N-dimethylamino)pyridine), inorganic bases (e.g. sodium carbonate, potassium carbonate, sodium hydride), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The present compound (I) (wherein $R^6$ is —COOH) can also be produced by hydrolyzing the compound (IV),

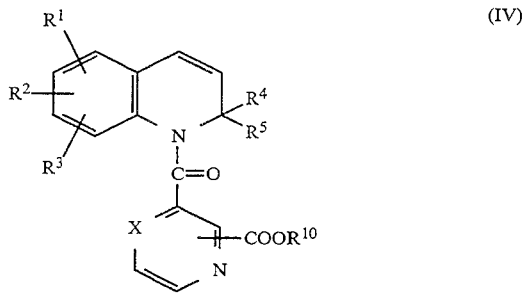
(IV)

wherein $R^1$, $R^2$, $R^3$, $R^4$, $R^5$ and X are each as defined above and $R^{10}$ represents a $C_1$–$C_6$ alkyl group; a $C_1$–$C_6$ alkenyl group; a $C_1$–$C_6$ alkynyl group; a halo-$C_1$–$C_6$ alkyl group; a halo-$C_1$–$C_6$ alkenyl group; a halo-$C_1$–$C_6$ alkynyl group; a $C_3$–$C_6$ cycloalkyl group; a $C_3$–$C_6$ cycloalkenyl group; a $C_1$–$C_6$ alkoxy-$C_1$–$C_6$ alkyl group; a $C_1$–$C_6$ alkylamino-$C_1$–$C_6$ alkyl group; a phenyl group optionally substituted with at least one member selected from the group consisting of halogen atoms and $C_1$–$C_6$ alkyl groups; a phenylalkyl group; a furylalkyl group; or a thienylalkyl group.

The reaction is usually carried out with or without a solvent in the presence of water, an acid or a base.

Generally, the reaction temperature ranges from 0° C. to the boiling point of the solvent. The reaction time ranges from 5 minutes to 24 hours. The amount of the water used is 1 to 1,000 equivalents based on 1 equivalent of the compound represented by the formula (IV), and the amount of acid or base used is 0.01–100 equivalents based on the same. Such a base includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc. Such an acid includes Lewis acids (e.g. $ZnCl_2$, $AlCl_3$), inorganic acids (e.g. HCl, $H_2SO_4$, $HNO_3$), organic acids (e.g. $CH_3COOH$, p-toluenesulfonic acid), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The present compound (I) [wherein $R^6$ represents

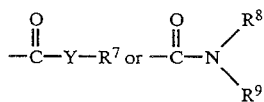

[wherein $R^7$, $R^8$, $R^9$ and Y are as defined above, provided that $R^6$ is not —COOH] can also be produced by reacting [reaction (i)] the present compound (I) (wherein $R^6$ represents —COOH) with an acid-halogenating agent or an active esterifying agent, and subsequently reacting [reaction (ii)] the resulting reaction product with an alcohol derivative represented by the formula (V),

H—Y—$R^7$ (V)

(wherein Y and $R^7$ are as defined above, provided that $R^7$ is not —OH) or an amine derivative represented by the formula (VI),

(VI)

(wherein $R^8$ and $R^9$ are as defined above).

In the above reaction (i), the acid-halogenating agent includes thionyl chloride, thionyl bromide, phosphorus trichloride, phosphorus tribromide, phosphorus pentachloride, phosphorus oxychloride, phosgene, oxalyl chloride, etc. The active esterifying agent includes N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolium trifluoroborate; N-ethyl-5-phenylisoxazolium-3'-sulfonate; etc.

By this reaction, a pyrimidine derivative represented by the formula (VII),

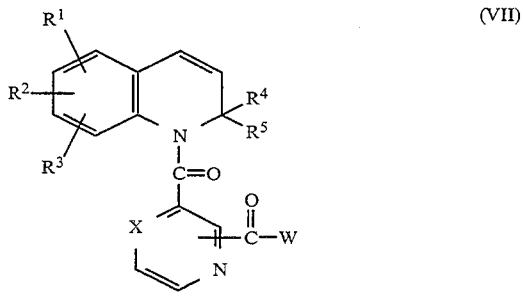
(VII)

wherein $R^1$, $R^2$, $R^3$, $R^4$, $R^5$ and X are as defined above, is produced in the reaction system.

In the above formula (VII), the substituent W represents a halogen atom when the acid-halogenating agent was used; W represents an N,N'-disubstituted-2-isoureide group when N,N'-disubstituted carbodiimide was used as the active esterifying agent; W represents an arylsulfonyloxy group when arylsulfonyl chloride was used as said agent; W represents an imidazolyl group when N,N'-carbonyldiimidazole was used as said agent; W represents an azide group when diphenylphosphorylazide was used as said agent; W represents an ethoxycarbonyloxy group when N-ethoxycarbonyl-2-ethoxy-1,2-dihydroquinoline was used as said agent; W represents 3-(N-ethylaminocarbonyl)-2-hydroxyphenoxy group when N-ethyl-2'-hydroxybenzisoxazolium trifluoroborate was used as said agent; and W represents a group

when N-ethyl-5-phenylisoxazolium-3'-sulfonate was used as said agent.

In the reaction system, W can also take a form of an acid anhydride represented by the formula,

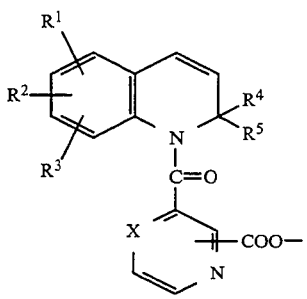

(wherein $R^1$, $R^2$, $R^3$, $R^4$, $R^5$ and X are as defined above).

The amount of the foregoing acid-halogenating agent or active esterifying agent used is usually 1 to 10 equivalents based on 1 equivalent of the present compound (I) (wherein $R^6$ represents —COOH).

The amount of the alcohol derivative of the formula (V) or the amine derivative of the formula (VI) used is usually 1 to 5 equivalents based on 1 equivalent of the present compound (I) (wherein $R^6$ represents —COOH).

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is 1 to 20 equivalents based on 1 equivalent of the present compound (I) (wherein $R^6$ represents —COOH).

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and mixtures thereof.

Generally, the reaction temperature ranges from 0° C. to the boiling point of the solvent in any of the reactions (i) and (ii). The reaction time ranges from 1 to 24 hours for each reaction, and from about 1 to about 48 hours for the reactions (i) through (ii).

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The dihydroquinoline derivative represented by the formula (II) can be produced according to Journal of Medicinal Chemistry, 16, 251 (1973). The present compounds (I) include their stereoisomers having a herbicidal activity.

The present compounds (I) have an excellent herbicidal activity and some of them have excellent selectivity between crops and weeds.

That is, the present compounds, when used for foliar treatment and soil treatment in upland fields, ridge or no-cultivating area, exhibit a herbicidal activity against various weeds, such as, Polygonaceae wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*)

Portulacaceae common purslane (*Portulaca oleracea*)

Caryophyllaceae common chickweed (*Stellaria media*)

Chenopodiaceae common lambsquarters (*Chenopodium album*), kochia (*Kochia scoparia*)

Amaranthaceae redroot pigweed (*Amaranthus retroflexus*), smooth pigweed (*Amaranthus hybridus*)

Cruciferae wild radish (*Raphanus raphanistrum*), wild mustard (*Brassica kaber*), shepherdspurse (*Capsella bursapastoris*)

Leguminosae hemp sesbania (*Sesbania exaltata*), sicklepod (*Cassia obtusifolia*), Florida beggarweed (*Desmodium tortuosum*), white clover (*Trifolium repens*)

Malvaceae velvetleaf (*Abutlion theophrasti*), prickly sida (*Sida spinosa*)

Violaceae field pansy (*Viola arvensis*), wild pansy (*Viola tricolor*)

Rubiaceae catchweed bedstraw (*Galium aparine*)

Convolvulaceae ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bingweed (*Convolvulus arvensis*)

Labiatae red deadnettle (*Lamium purpureum*), henbit (*Lamium amplexicaule*)

Solanaceae jimsonweed (*Datula stramonium*), black nightshade (*Solanum nigram*)

Scrophulariaceae birdseye speedwell (*Veronica persica*), ivyleaf speedwell (*Veronica hederaefolia*)

Compositae common cocklebur (*Xanthium pensylvanicum*), common sunflower (*Helianthus annuus*), scentless chamomile (*Matricaria inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*)

Boraginaceae field forget-me-not (*Myosotis arvensis*)

Asclepiadaceae common milkweed (*Asclepias syriaca*)

Euphorbiaceae sun spurge (*Euphorbia helioscopia*), spotted spurge (*Euphorbia maculata*)

Gramineae barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Arena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceae common dayflower (*Commelina communis*)

Equisetaceae field horsetail (*Equisetum arvense*), and

Cyperaceae rice flatsedge (*Cyperus iria*), purple nutsedge (*Cyperus rotundus*), yellow nutsedge (*Cyperus esculentus*)

In addition, some of the present compounds give such no phytotoxicity as becoming a problem to main crops such as corn (*Zea mays*), wheat (*Triticum aestivum*), barley (*Hordeum vulgare*), rice (*Oryza sativa*), soybean (*Glycine max*), cotton (Gossypium spp), sugar beet (*Beta vulgaris*), peanut (*Arachis hypogaea*), sunflower (*Helianthus annuus*), rape (*Brassica napus*), etc. and horticultural crops such as flower, ornamental plants and vegetables.

The present compound (I) also can safely be used for no-till cultivation in soybean fields, peanut fields, corn fields, etc., and some of them give such no phytotoxicity as becoming a problem to crops.

In flooding treatment in paddy fields, the present compounds exhibit a herbicidal activity against weeds such as Gramineae

*Echinochloa oryzicola*

Scrophulariaceae common falsepimpernel (*Lindernia procumbens*)

Lythraceae

*Rotala indica, Ammannia multiflora*

Elatinaceae

*Elatine triandra*

Cyperaceae smallflower umbrellaplant (*Cyperus difformis*), Scirpus juncoides, needle spikerush (*Eleocharis acicularis*), *Cyperus serotinus*, Eleocharis kuroguwai Pontederiaceae

*Monochoria vaginalis*

Alismataceae

*Sagittaria pygmaea, Sagittaria trifolia, Alisma canaliculatum*

Potamogetonaceae roundleaf pondweed (*Potamogeton distinctus*), and

Umbelliferae

*Qenanthe javanica*

Some of the present compound give such no phytotoxicity as becoming a problem to a transplanted rice plant or a direct seeded rice plant in paddy field.

The present compound (I) can be used as an active ingredient for herbicides used in orchards, pastures, turfs, forests, afforestation area and non-agricultural fields (e.g. water way, canal), etc.

When the present compound (I) is used as an active ingredient for herbicides, it is usually formulated before use into emulsifiable concentrates, wettable powders, suspension formulations, granules, water-dispersible granules, etc. by mixing with solid carriers, liquid carriers, surface active agents or other auxiliaries for formulation.

The content of the compound (I) as an active ingredient in these preparations is normally within a range of about 0.03 to 75% by weight, preferably of about 0.05 to 70% by weight.

Examples of the solid carriers are fine powders or granules of kaolin clay, attapulgite clay, bentonite, terra alba, pyrophyllite, talc, diatomaceous earth, calcite, walnut shell powders, urea, ammonium sulfate, synthetic hydrated silicon dioxide, etc.

Examples of the liquid carriers are aromatic hydrocarbons (e.g. xylene, alkylbenzene, methylnaphthalene, phenylquinolylethane), alcohols (e.g. isopropanol, ethylene glycol), esters (e.g. dialkyl phthalate), ketones (e.g. acetone, cyclohexanone, isophorone), mineral oils (e.g. machine oil), vegetable oils (e.g. soybean oil, cotton seed oil), dimethyl sulfoxide, N,N-dimethylformamide, acetonitrile, N-methylpyrrolidone, water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc.

Examples of other auxiliary agents for formulation are lignosulfonates, alginates, polyvinyl alcohol, gum arabic, CMC (carboxymethyl cellulose), PAP (isopropyl acid phosphate), etc.

The present compound (I) is usually formulated and used in soil treatment, foliar treatment or flooding treatment before or after emergence of weeds. The soil treatment includes soil surface treatment, soil incorporation treatment, etc. The foliar treatment includes, in addition to treatment of plants from above, directed treatment in which treatment is limited to weeds only so as not to adhere to crops.

Build-up of the herbicidal activity of the present compound (I) can be expected by using them in mixture with other herbicides. Further, the present compound (I) can also be used in mixture with insecticides, acaricides, nematocides, fungicides, bacteriocides, plant growth regulators, fertilizers, soil improvers, etc.

When the present compound (I) is used as an active ingredient for herbicides, their dosage rate varies with weather conditions, preparation forms, when, how and where the treatment is carried out, weeds species to be controlled, crops species to be protected, etc. Usually, however, the dosage rate is from 10 grams to 10000 grams of the active ingredient per hectare, preferably from 20 grams to 8000 grams of the active ingredient per hectare.

The herbicidal composition of the present invention formulated into the form of an emulsifiable concentrate, a wettable powder, a suspension formulation or water dispersible granules may ordinarily be employed by diluting it with water at a volume of about 10 to 1000 liters per hectare (if necessary, adjuvants such as a spreading agent are added to the water). The granules and some suspension formulations are usually applied without being diluted.

The adjuvants include, in addition to the foregoing surface active agents, substances such as polyoxyethylene resin acids (esters), lignosulfonates, abietates, dinaphthylmethanedisulfonates and vegetable oils (e.g. crop oil concentrate, soybean oil, corn oil, cotton seed oil, sunflower oil).

The present invention will be illustrated in more detail with reference to the following production examples, formulation examples and test examples, which are not however to be interpreted as limiting the invention thereto.

First, production examples for the present compound (I) are shown.

PRODUCTION EXAMPLE 1

5.34 g of nicotinic acid chloride hydrochloride was suspended in 50 ml of methylene chloride and 7.56 g of triethylamine was added thereto. After the resulting suspension was stirred at room temperature for 30 minutes, 3.88 g of 6-chloro-2,2-dimethyl-1,2-dihydroquinoline dissolved in 20 ml of methylene chloride was added thereto. Further, 1.00 g of 4-dimethylaminopyridine was added thereto. After refluxing the resulting solution mixture for 7 hours, the reaction solution was poured into water and extracted with ethyl acetate. The organic layer separated from the aqueous layer was washed with water and dried over anhydrous magnesium sulfate. The solvent was distilled off under reduced pressure, and the residue obtained was subjected to thin-layer chromatography (silica gel; ethyl acetate/hexane 1:1 (V/V)) to obtain 1.01 g of 6-chloro-2,2-dimethyl-1-nicotinoyl-1,2-dihydroquinoline (the present compound (1)).

$H^1$—NMR (CDCl$_3$) $\sigma$; 1.67 (s, 6H) 5.92 (d, 1H, J=10.0 Hz) 6.48 (d, 1H, J=10.0 Hz) 6.25–7.44 (m, 4H) 7.85–8.07 (m, 1H) 8.66–8.86 (m, 2H).

PRODUCTION EXAMPLE 2

1.43 g of pyrazinecarboxylic acid chloride was dissolved in 20 ml of methylene chloride and 1.21 g of triethylamine was added thereto. After the resulting solution was stirred at room temperature for 30 minutes, 1.73 g of 6-methyl-2,2-dimethyl-1,2-dihydroquinoline dissolved in 5 ml of methylene chloride was added thereto. Further, 0.3 g of 4-dimethylaminopyridine was added thereto. After refluxing the resulting mixture for 7 hours, the reaction solution was poured into water and extracted with ethyl acetate. The organic layer separated from the aqueous layer was washed with water and dried over anhydrous magnesium sulfate. The solvent was distilled off under reduced pressure and the residue obtained was subjected to thin-layer chromatography (silica gel; ethyl acetate/hexane 1:1 (V/V)) to obtain 0.76 g of 6-methyl-2,2-dimethyl-1-pyradinecarbonyl-1,2-dihydroquinoline (the present compound (7)).

$H^1$—NMR (CDCl$_3$) $\sigma$; 1.63 (s, 6H) 2.08 (s, 3H) 5.63 (d, 1H, J=10.0 Hz) 6.23 (d, 1H, J=10.0 Hz) 5.97–8.00 (m, 3H) 8.23 (s, 2H) 8.50 (s, 1H).

PRODUCTION EXAMPLE 3

To 20 ml of aqueous 1N sodium hydroxide solution combined with 20 ml of methanol, was added 3.56 g of the present compound (28). After stirring the mixture with heating at 60°–80° C. for one hour, and after distilling most of the methanol off under reduced pressure, the residue was poured into water and the solution was made weekly acidic with conc. hydrochloric acid. The resulting precipitate was separated by filtration through a glass filter and dried at 50° C. under reduced pressure to obtain 2.90 g of 6-chloro-2,2-dimethyl-1-(4-carboxynicotinoyl)-1,2-dihydroquinoline (the present compound (30)).

$H^1$—NMR (DMSO-d$_6$) $\sigma$; 1.62 (s, 6H) 5.90 (d, 1H, J=10.0 Hz) 6.48 (d, 1H, J=10.0 Hz) 6.65–8.17 (m, 3H) 7.58 (d, 1H, J=5.0 Hz) 8.20 (s, 1H) 8.63 (d, 1H, J=5.0 Hz).

PRODUCTION EXAMPLE 4

1.03 g of 6-chloro-2,2-dimethyl-1-(4-carboxynicotinoyl)-1,2-dihydroquinoline (the present compound (30)) was dissolved in 30 ml of tetrahydrofuran and 0.98 g of mesithylene sulfonylchloride and 0.73 g of 1-methylimidazole were added thereto. After the resulting solution was stirred at room temperature for 10 minutes, 0.22 g of monomethylamine hydrochloride and 0.34 g of triethylamine were added thereto. After the resulting solution was stirred at room temperature for 15 minutes, the reaction solution was poured into water and extracted with ethyl acetate. The organic layer separated from the aqueous layer was washed with water and dried over anhydrous magnesium sulfate. The residue obtained was subjected to thin-layer chromatography (silica gel; chloroform/methanol 9:1 (V/V)) to obtain 0.80 g of 6-chloro-2,2-dimethyl-1-

(4—N-methylcarbamoylnicotinoyl)-1,2-dihydroquinoline (the present compound (72)).

H$^1$—NMR (CDCl$_3$) σ; 1.66 (s, 6H) 3.05 (d, 3H, J=4.89 Hz) 5.86 (d, 1H, J=9.68 Hz) 6.36 (d, 1H, J=9.68 Hz) 6.50 (br.d 1H, J=4.89 Hz) 6.75 (dd, 1H, J$_1$=8.57 Hz, J$_2$=2.45 Hz) 6.98 (d, 1H, J=2.45 Hz) 7.09 (d, 1H, J=8.57 Hz) 7.33 (d, 1H, J=4.96 Hz) 8.30 (s, 1H) 8.56 (d, 1H, J=4.96 Hz).

Table 1 illustrates examples of the compound (I) which can be produced by the above procedure of Production Examples 1 and 2.

Compound (I) (wherein R$^6$ is —COOH) can also be prepared according to the procedure of Production Example 3.

Compound (I) (wherein R$^6$ is

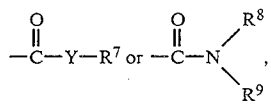

proviso R$^6$ is not —COOH) can also be prepared according to the procedure of Production Example 4.

TABLE 1

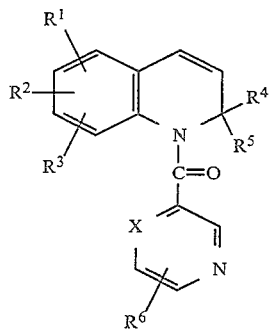

| Compound No. | R$^1$ | R$^2$ | R$^3$ | R$^4$ | R$^5$ | R$^6$ | X |
|---|---|---|---|---|---|---|---|
| (1) | 6-Cl | H | H | CH$_3$ | CH$_3$ | H | CH |
| (2) | 6-Cl | H | H | CH$_3$ | CH$_3$ | H | N |
| (3) | 6-Cl | H | H | CH$_3$ | CH$_3$ | 2-Cl | CH |
| (4) | 6-Cl | H | H | CH$_3$ | CH$_3$ | 5-Br | CH |
| (5) | 6-OCH$_3$ | H | H | CH$_3$ | CH$_3$ | H | CH |
| (6) | 6-CH$_3$ | H | H | CH$_3$ | CH$_3$ | H | CH |
| (7) | 6-CH$_3$ | H | H | CH$_3$ | CH$_3$ | H | N |
| (8) | 6-OCH$_3$ | H | H | CH$_3$ | CH$_3$ | H | N |
| (9) | 8-OCH$_3$ | H | H | CH$_3$ | CH$_3$ | H | CH |
| (10) | 6-F | H | H | CH$_3$ | CH$_3$ | H | CH |
| (11) | 6-F | H | H | CH$_3$ | CH$_3$ | H | N |
| (12) | 8-OCH$_3$ | H | H | CH$_3$ | CH$_3$ | H | N |
| (13) | H | H | H | CH$_3$ | CH$_3$ | H | CH |
| (14) | H | H | H | CH$_3$ | CH$_3$ | H | N |
| (15) | 6-CF$_3$ | H | H | CH$_3$ | CH$_3$ | H | CH |
| (16) | 6-OCF$_3$ | H | H | CH$_3$ | CH$_3$ | H | CH |
| (17) | 7-CH$_3$ | 8-CH$_3$ | H | CH$_3$ | CH$_3$ | H | CH |
| (18) | 6-CH$_3$ | 8-CH$_3$ | H | CH$_3$ | CH$_3$ | H | CH |
| (19) | 5-CH$_3$ | H | H | CH$_3$ | CH$_3$ | H | CH |
| (20) | 7-CH$_3$ | H | H | CH$_3$ | CH$_3$ | H | CH |
| (21) | 6-Ph | H | H | CH$_3$ | CH$_3$ | H | CH |
| (22) | 6-OPh | H | H | CH$_3$ | CH$_3$ | H | CH |
| (23) | 5-CH$_3$ | 7-CH$_3$ | H | CH$_3$ | CH$_3$ | H | CH |
| (24) | 6-CH$_3$ | 7-CH$_3$ | H | CH$_3$ | CH$_3$ | H | CH |
| (25) | 5-CH$_3$ | 6-CH$_3$ | H | CH$_3$ | CH$_3$ | H | CH |
| (26) | 5-OCH$_3$ | H | H | CH$_3$ | CH$_3$ | H | CH |
| (27) | 8-F | H | H | CH$_3$ | CH$_3$ | H | CH |
| (28) | 6-Cl | H | H | CH$_3$ | CH$_3$ | 4-COOCH$_3$ | CH |
| (29) | 6-Cl | H | H | CH$_3$ | CH$_3$ | 4-Cl | CH |
| (30) | 6-Cl | H | H | CH$_3$ | CH$_3$ | 4-COOH | CH |
| (31) | 6-Cl | H | H | CH$_3$ | CH$_3$ | 4-COOC$_2$H$_5$ | CH |
| (32) | 6-Cl | H | H | CH$_3$ | CH$_3$ | 4-COOCH$_2$CF$_3$ | CH |
| (33) | 6-Cl | H | H | CH$_3$ | CH$_3$ | 4-COOCH$_2$CH$_2$Cl | CH |
| (34) | 6-Cl | H | H | CH$_3$ | CH$_3$ | 4-COOC$_3$H$_7$(n) | CH |
| (35) | 6-Cl | H | H | CH$_3$ | CH$_3$ | 4-COOCH$_2$CH=CH$_2$ | CH |
| (36) | 6-Cl | H | H | CH$_3$ | CH$_3$ | 4-COOCH$_2$C≡CH | CH |
| (37) | 6-Cl | H | H | CH$_3$ | CH$_3$ | 4-COOC$_3$H$_7$(iso) | CH |
| (38) | 6-Cl | H | H | CH$_3$ | CH$_3$ | 4-COOCH$_2$CH=CH(CH$_3$) | CH |
| (39) | 6-Cl | H | H | CH$_3$ | CH$_3$ | 4-COOCH$_2$CH=CHCl | CH |
| (40) | 6-Cl | H | H | CH$_3$ | CH$_3$ | 4-COOC$_4$H$_9$(n) | CH |
| (41) | 6-Cl | H | H | CH$_3$ | CH$_3$ | 4-COOC$_4$H$_9$(iso) | CH |
| (42) | 6-Cl | H | H | CH$_3$ | CH$_3$ | 4-COOCH(CH$_3$)CH=CH$_2$ | CH |
| (43) | 6-Cl | H | H | CH$_3$ | CH$_3$ | 4-COOCH(CH$_3$)C≡CH | CH |
| (44) | 6-Cl | H | H | CH$_3$ | CH$_3$ | 4-COOCH$_2$CH(CH$_3$)=CH$_2$ | CH |
| (45) | 6-Cl | H | H | CH$_3$ | CH$_3$ | 4-COOC$_4$H$_9$(t) | CH |
| (46) | 6-Cl | H | H | CH$_3$ | CH$_3$ | 4-COOCH(C$_2$H$_5$)$_2$ | CH |
| (47) | 6-Cl | H | H | CH$_3$ | CH$_3$ | 4-COOCH$_2$CH=C(CH$_3$)$_2$ | CH |
| (48) | 6-Cl | H | H | CH$_3$ | CH$_3$ | 4-COOC(CH$_3$)$_2$CH=CH$_2$ | CH |
| (49) | 6-Cl | H | H | CH$_3$ | CH$_3$ | 4-COOC$_5$H$_9$(cyclo) | CH |
| (50) | 6-Cl | H | H | CH$_3$ | CH$_3$ | 4-COOC$_6$H$_{13}$(n) | CH |

TABLE 1-continued

| Compound No. | R¹ | R² | R³ | R⁴ | R⁵ | R⁶ | X |
|---|---|---|---|---|---|---|---|
| (51) | 6-Cl | H | H | CH₃ | CH₃ | 4-COOC₆H₁₁(cyclo) | CH |
| (52) | 6-Cl | H | H | CH₃ | CH₃ | 4-COOC₇H₁₅(n) | CH |
| (53) | 6-Cl | H | H | CH₃ | CH₃ | 4-COOCH₂CH₂OCH₃ | CH |
| (54) | 6-Cl | H | H | CH₃ | CH₃ | 4-COOPh | CH |
| (55) | 6-Cl | H | H | CH₃ | CH₃ | 4-COO-(2-Cl-phenyl) | CH |
| (56) | 6-Cl | H | H | CH₃ | CH₃ | 4-COO-(3-Cl-phenyl) | CH |
| (57) | 6-Cl | H | H | CH₃ | CH₃ | 4-COO-(4-Cl-phenyl) | CH |
| (58) | 6-Cl | H | H | CH₃ | CH₃ | 4-COO-(2-F-phenyl) | CH |
| (59) | 6-Cl | H | H | CH₃ | CH₃ | 4-COO-(3-F-phenyl) | CH |
| (60) | 6-Cl | H | H | CH₃ | CH₃ | 4-COO-(2-C₂H₅O₂C-phenyl) | CH |
| (61) | 6-Cl | H | H | CH₃ | CH₃ | 4-COOCH₂Ph | CH |
| (62) | 6-Cl | H | H | CH₃ | CH₃ | 4-COOCH₂-(2-thienyl) | CH |
| (63) | 6-Cl | H | H | CH₃ | CH₃ | 4-COOCH₂-(3-furyl) | CH |
| (64) | 6-Cl | H | H | CH₃ | CH₃ | 4-COOCH₂-(2-furyl) | CH |

TABLE 1-continued

| Compound No. | $R^1$ | $R^2$ | $R^3$ | $R^4$ | $R^5$ | $R^6$ | X |
|---|---|---|---|---|---|---|---|
| (65) | 6-Cl | H | H | $CH_3$ | $CH_3$ | 4-COO—(cyclohexyl) | CH |
| (66) | 6-Cl | H | H | $CH_3$ | $CH_3$ | 4-COOCH$_2$CH$_2$N(CH$_3$)$_2$ | CH |
| (67) | 6-Cl | H | H | $CH_3$ | $CH_3$ | 4-COON(CH$_3$)$_2$ | CH |
| (68) | 6-Cl | H | H | $CH_3$ | $CH_3$ | 4-COON(C$_2$H$_5$)$_2$ | CH |
| (69) | 6-Cl | H | H | $CH_3$ | $CH_3$ | 4-COON=C(CH$_3$)$_2$ | CH |
| (70) | 6-Cl | H | H | $CH_3$ | $CH_3$ | 4-CONH$_2$ | CH |
| (71) | 6-Cl | H | H | $CH_3$ | $CH_3$ | 4-CONHNH$_2$ | CH |
| (72) | 6-Cl | H | H | $CH_3$ | $CH_3$ | 4-CONHCH$_3$ | CH |
| (73) | 6-Cl | H | H | $CH_3$ | $CH_3$ | 4-CONHCH$_2$CH=CH$_2$ | CH |
| (74) | 6-Cl | H | H | $CH_3$ | $CH_3$ | 4-CONHCH$_2$C≡CH | CH |
| (75) | 6-Cl | H | H | $CH_3$ | $CH_3$ | 4-CONHC$_3$H$_7$(iso) | CH |
| (76) | 6-Cl | H | H | $CH_3$ | $CH_3$ | 4-CON(C$_2$H$_5$)$_2$ | CH |
| (77) | 6-Cl | H | H | $CH_3$ | $CH_3$ | 4-CONHPh | CH |
| (78) | 6-Cl | H | H | $CH_3$ | $CH_3$ | 4-COSCH$_3$ | CH |
| (79) | 6-Cl | H | H | $CH_3$ | $CH_3$ | 4-NH$_2$ | CH |
| (80) | 6-Cl | H | H | $CH_3$ | $CH_3$ | 4-NHCO$_2$CH$_3$ | CH |
| (81) | 6-Cl | H | H | $CH_3$ | $CH_3$ | 4-CN | CH |
| (82) | 6-Br | H | H | $CH_3$ | $CH_3$ | H | CH |
| (83) | 6-Br | H | H | $CH_3$ | $CH_3$ | 4-COOCH$_3$ | CH |
| (84) | 6-Br | H | H | $CH_3$ | $CH_3$ | 4-COOC$_3$H$_7$(iso) | CH |
| (85) | H | H | H | $CH_3$ | $CH_3$ | 4-COOCH$_3$ | CH |
| (86) | H | H | H | $CH_3$ | $CH_3$ | 4-COOC$_2$H$_5$ | CH |
| (87) | H | H | H | $CH_3$ | $CH_3$ | 4-COOC$_3$H$_7$(iso) | CH |
| (88) | H | H | H | $CH_3$ | $CH_3$ | 4-COOC$_6$H$_{11}$(cyclo) | CH |
| (89) | H | H | H | $CH_3$ | $CH_3$ | 4-COOC$_6$H$_{13}$(n) | CH |
| (90) | 6-CH$_3$ | H | H | $CH_3$ | $CH_3$ | 4-COOCH$_3$ | CH |
| (91) | 6-CH$_3$ | H | H | $CH_3$ | $CH_3$ | 4-COOC$_2$H$_5$ | CH |
| (92) | 6-CH$_3$ | H | H | $CH_3$ | $CH_3$ | 4-COOC$_3$H$_7$(iso) | CH |
| (93) | 6-OCH$_3$ | H | H | $CH_3$ | $CH_3$ | 4-COOCH$_3$ | CH |
| (94) | 6-OCH$_3$ | H | H | $CH_3$ | $CH_3$ | 4-COOC$_2$H$_5$ | CH |
| (95) | 6-OCH$_3$ | H | H | $CH_3$ | $CH_3$ | 4-COOC$_3$H$_7$(iso) | CH |
| (96) | 6-SCH$_3$ | H | H | $CH_3$ | $CH_3$ | H | CH |
| (97) | 6-Ph | H | H | $CH_3$ | $CH_3$ | 4-COOH | CH |
| (98) | 6-Ph | H | H | $CH_3$ | $CH_3$ | 4-COOCH$_3$ | CH |
| (99) | 6-Ph | H | H | $CH_3$ | $CH_3$ | 4-COOC$_2$H$_5$ | CH |
| (100) | 6-Ph | H | H | $CH_3$ | $CH_3$ | 4-COOC$_3$H$_7$(iso) | CH |
| (101) | 6-Ph | H | H | $CH_3$ | $CH_3$ | 4-COOC$_4$H$_9$(n) | CH |
| (102) | 6-Ph | H | H | $CH_3$ | $CH_3$ | 4-COOPh | CH |
| (103) | 6-Ph | H | H | $CH_3$ | $CH_3$ | 4-COOCH$_2$Ph | CH |
| (104) | 6-F | H | H | $CH_3$ | $CH_3$ | 4-COOH | CH |
| (105) | 6-F | H | H | $CH_3$ | $CH_3$ | 4-COOCH$_3$ | CH |
| (106) | 6-F | H | H | $CH_3$ | $CH_3$ | 4-COOC$_2$H$_5$ | CH |
| (107) | 6-F | H | H | $CH_3$ | $CH_3$ | 4-COOC$_3$H$_7$(n) | CH |
| (108) | 6-F | H | H | $CH_3$ | $CH_3$ | 4-COOC$_3$H$_7$(iso) | CH |
| (109) | 6-F | H | H | $CH_3$ | $CH_3$ | 4-COOC$_4$H$_9$(n) | CH |
| (110) | 6-F | H | H | $CH_3$ | $CH_3$ | 4-COOC$_6$H$_{13}$(n) | CH |
| (111) | 6-F | H | H | $CH_3$ | $CH_3$ | 4-COOPh | CH |
| (112) | 6-F | H | H | $CH_3$ | $CH_3$ | 4-COOC$_6$H$_{11}$(cyclo) | CH |
| (113) | 6-C$_3$H$_7$(iso) | H | H | $CH_3$ | $CH_3$ | H | CH |
| (114) | 6-C$_4$H$_9$(n) | H | H | $CH_3$ | $CH_3$ | H | CH |
| (115) | 6-C$_4$H$_9$(iso) | H | H | $CH_3$ | $CH_3$ | H | CH |
| (116) | 6-CO$_2$C$_2$H$_5$ | H | H | $CH_3$ | $CH_3$ | H | CH |
| (117) | 6-N(CH$_3$)$_2$ | H | H | $CH_3$ | $CH_3$ | H | CH |
| (118) | H | H | H | $CH_3$ | $CH_3$ | 4-Cl | CH |
| (119) | H | H | H | $CH_3$ | $CH_3$ | 4-Br | CH |
| (120) | H | H | H | $CH_3$ | $CH_3$ | 4-COOCH$_3$ | CH |
| (121) | H | H | H | $CH_3$ | $CH_3$ | 4-COOC$_2$H$_5$ | CH |
| (122) | H | H | H | $CH_3$ | $CH_3$ | 4-COOC$_3$H$_7$(iso) | CH |

TABLE 1-continued

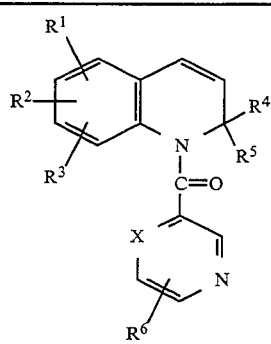

| Compound No. | R¹ | R² | R³ | R⁴ | R⁵ | R⁶ | X |
|---|---|---|---|---|---|---|---|
| (123) | 5-CH₃ | H | H | CH₃ | CH₃ | H | N |
| (124) | 5-CH₃ | H | H | CH₃ | CH₃ | 4-Cl | CH |
| (125) | 5-CH₃ | H | H | CH₃ | CH₃ | 4-COOCH₃ | CH |
| (126) | 6-CH₃ | H | H | CH₃ | CH₃ | 4-Cl | CH |
| (127) | 7-CH₃ | H | H | CH₃ | CH₃ | 4-COOCH₃ | CH |
| (128) | 8-CH₃ | H | H | CH₃ | CH₃ | 4-Cl | CH |
| (129) | 8-CH₃ | H | H | CH₃ | CH₃ | 4-COOCH₃ | CH |
| (130) | 6-C₂H₅ | H | H | CH₃ | CH₃ | 4-Cl | CH |
| (131) | 6-C₂H₅ | H | H | CH₃ | CH₃ | 4-COOCH₃ | CH |
| (132) | 6-C₃H₇(n) | H | H | CH₃ | CH₃ | H | CH |
| (133) | 6-C₃H₇(iso) | H | H | CH₃ | CH₃ | H | CH |
| (134) | 6-CO₂C₂H₅ | H | H | CH₃ | CH₃ | 4-COOCH₃ | CH |
| (135) | 6-N(CH₃)₂ | H | H | CH₃ | CH₃ | 4-COOCH₃ | CH |
| (136) | 5-CH₃ | 6-CH₃ | H | CH₃ | CH₃ | 4-Cl | CH |
| (137) | 5-CH₃ | 7-CH₃ | H | CH₃ | CH₃ | 4-COOCH₃ | CH |
| (138) | 5-CH₃ | 8-CH₃ | H | CH₃ | CH₃ | H | CH |
| (139) | 6-CH₃ | 7-CH₃ | H | CH₃ | CH₃ | 4-COOCH₃ | CH |
| (140) | 6-CH₃ | 8-CH₃ | H | CH₃ | CH₃ | 4-COOCH₃ | CH |
| (141) | 5-CH₃ | 6-CH₃ | 8-CH₃ | CH₃ | CH₃ | H | CH |
| (142) | 5-CH₃ | 6-CH₃ | 8-CH₃ | CH₃ | CH₃ | 4-Cl | CH |
| (143) | 5-CH₃ | 6-CH₃ | 8-CH₃ | CH₃ | CH₃ | 4-COOCH₃ | CH |
| (144) | 5-F | H | H | CH₃ | CH₃ | H | CH |
| (145) | 5-F | H | H | CH₃ | CH₃ | 4-Cl | CH |
| (146) | 6-F | H | H | CH₃ | CH₃ | 4-Cl | CH |
| (147) | 6-F | H | H | CH₃ | CH₃ | 4-COOCH₃ | CH |
| (148) | 7-F | H | H | CH₃ | CH₃ | 4-Cl | CH |
| (149) | 7-F | H | H | CH₃ | CH₃ | 4-COOCH₃ | CH |
| (150) | 8-F | H | H | CH₃ | CH₃ | 4-Cl | CH |
| (151) | 8-F | H | H | CH₃ | CH₃ | 4-COOCH₃ | CH |
| (152) | 5-Cl | H | H | CH₃ | CH₃ | H | CH |
| (153) | 5-Cl | H | H | CH₃ | CH₃ | 4-Cl | CH |
| (154) | 6-Cl | H | H | CH₃ | C₂H₅ | H | CH |
| (155) | 6-Cl | H | H | CH₃ | C₂H₅ | 4-Cl | CH |
| (156) | 6-Cl | H | H | CH₃ | C₂H₅ | 4-COOCH₃ | CH |
| (157) | 8-Cl | H | H | CH₃ | CH₃ | 4-Cl | CH |
| (158) | 8-Cl | H | H | CH₃ | CH₃ | 4-COOCH₃ | CH |
| (159) | 6-Br | H | H | CH₃ | CH₃ | H | CH |
| (160) | 6-Br | H | H | CH₃ | CH₃ | 4-Cl | CH |
| (161) | 6-Br | H | H | CH₃ | CH₃ | 4-COOCH₃ | CH |
| (162) | 6-Cl | 8-F | H | CH₃ | CH₃ | H | CH |
| (163) | 6-Cl | 8-F | H | CH₃ | CH₃ | H | N |
| (164) | 6-Cl | 8-F | H | CH₃ | CH₃ | 4-Cl | CH |
| (165) | 6-Cl | 8-F | H | CH₃ | CH₃ | 4-COOCH₃ | CH |
| (166) | 6-F | 8-Cl | H | CH₃ | CH₃ | H | CH |
| (167) | 6-F | 8-Cl | H | CH₃ | CH₃ | H | N |
| (168) | 6-F | 8-Cl | H | CH₃ | CH₃ | 4-Cl | CH |
| (169) | 6-F | 8-Cl | H | CH₃ | CH₃ | 4-COOCH₃ | CH |
| (170) | 5-OCH₃ | H | H | CH₃ | CH₃ | 4-Cl | CH |
| (171) | 5-OCH₃ | H | H | CH₃ | CH₃ | 4-COOCH₃ | CH |
| (172) | 6-OCH₃ | H | H | CH₃ | CH₃ | 4-Cl | CH |
| (173) | 6-OCH₃ | H | H | CH₃ | CH₃ | 4-COOCH₃ | CH |
| (174) | 7-OCH₃ | H | H | CH₃ | CH₃ | 4-Cl | CH |
| (175) | 7-OCH₃ | H | H | CH₃ | CH₃ | 4-COOCH₃ | CH |
| (176) | 8-OCH₃ | H | H | CH₃ | CH₃ | 4-Cl | CH |
| (177) | 8-OCH₃ | H | H | CH₃ | CH₃ | 4-COOCH₃ | CH |
| (178) | 6-CHF₂ | H | H | CH₃ | CH₃ | 4-Cl | CH |
| (179) | 6-CHF₂ | H | H | CH₃ | CH₃ | 4-COOCH₃ | CH |
| (180) | 6-CF₃ | H | H | CH₃ | CH₃ | 4-Cl | CH |
| (181) | 6-CF₃ | H | H | CH₃ | CH₃ | 4-COOCH₃ | CH |
| (182) | 6-OCF₃ | H | H | CH₃ | CH₃ | 4-Cl | CH |
| (183) | 6-OCF₃ | H | H | CH₃ | CH₃ | 4-COOCH₃ | CH |
| (184) | 6-OCF₂CF₂H | H | H | CH₃ | CH₃ | 4-Cl | CH |
| (185) | 6-OCF₂CF₂H | H | H | CH₃ | CH₃ | 4-COOCH₃ | CH |
| (186) | 6-Ph | H | H | CH₃ | CH₃ | H | N |

TABLE 1-continued

| Compound No. | R¹ | R² | R³ | R⁴ | R⁵ | R⁶ | X |
|---|---|---|---|---|---|---|---|
| (187) | 6-Ph | H | H | CH₃ | CH₃ | 4-Cl | CH |
| (188) | 6-Ph | H | H | CH₃ | CH₃ | 4-COOCH₃ | CH |
| (189) | 6-OPh | H | H | CH₃ | CH₃ | H | N |
| (190) | 6-OPh | H | H | CH₃ | CH₃ | 4-Cl | CH |
| (191) | 6-OPh | H | H | CH₃ | CH₃ | 4-COOCH₃ | CH |
| (192) | 6-Cl | H | H | CH₃ | CH₃ | 4-COOCH₂CH₂F | CH |
| (193) | 6-Cl | H | H | CH₃ | CH₃ | 4-COOCH₂CH₂Br | CH |
| (194) | 6-Cl | H | H | CH₃ | CH₃ | 4-COOCH₂CHF₂ | CH |
| (195) | 6-Cl | H | H | CH₃ | CH₃ | 4-COOCH₂CHCl₂ | CH |
| (196) | 6-Cl | H | H | CH₃ | CH₃ | 4-COOCH₂CH=CCl₂ | CH |
| (197) | 6-Cl | H | H | CH₃ | CH₃ | 4-COOCH₂CCl=CH₂ | CH |
| (198) | 6-Cl | H | H | CH₃ | CH₃ | 4-COOCH₂CH=CHF | CH |
| (199) | 6-Cl | H | H | CH₃ | CH₃ | 4-COOCH₂CH=CF₂ | CH |
| (200) | 6-Cl | H | H | CH₃ | CH₃ | 4-COOCH₂CF=CH₂ | CH |
| (201) | 6-Cl | H | H | CH₃ | CH₃ | 4-COOCH(CH₃)=CH₂ | CH |
| (202) | 6-Cl | H | H | CH₃ | CH₃ | 4-COOC₄H₉(sec) | CH |
| (203) | 6-Cl | H | H | CH₃ | CH₃ | 4-COOC₄H₇(cyclo) | CH |
| (204) | 6-Cl | H | H | CH₃ | CH₃ | 4-COOC₃H₅(cyclo) | CH |
| (205) | 6-Cl | H | H | CH₃ | CH₃ | 4-COOC₅H₁₁(n) | CH |
| (206) | 6-Cl | H | H | CH₃ | CH₃ | 4-COOCH(CH₃)C₄H₉ | CH |
| (207) | 6-Cl | H | H | CH₃ | CH₃ | 4-COOCH₂CH₂OC₂H₅ | CH |
| (208) | 6-Cl | H | H | CH₃ | CH₃ | 4-COO-(4-F-phenyl) | CH |
| (209) | 6-Cl | H | H | CH₃ | CH₃ | 4-COOCH₂-(2-Cl-phenyl) | CH |
| (210) | 6-Cl | H | H | CH₃ | CH₃ | 4-COOCH₂-(3-CH₃-phenyl) | CH |
| (211) | 6-Cl | H | H | CH₃ | CH₃ | 4-COO-(cyclopentenyl) | CH |
| (212) | 6-Cl | H | H | CH₃ | CH₃ | 4-COSC₂H₅ | CH |
| (213) | 6-Cl | H | H | CH₃ | CH₃ | 4-COSCH₂CH=CH₂ | CH |
| (214) | 6-Cl | H | H | CH₃ | CH₃ | 4-COSCH₂CH₂Cl | CH |
| (215) | 6-Cl | H | H | CH₃ | CH₃ | 4-COSCH₂CH₂OCH₃ | CH |
| (216) | 6-Cl | H | H | CH₃ | CH₃ | 4-COSC₃H₇(n) | CH |
| (217) | 6-Cl | H | H | CH₃ | CH₃ | 4-COSC₃H₇(n) | N |
| (218) | 6-Cl | H | H | CH₃ | CH₃ | 4-COSC₄H₉(n) | CH |
| (219) | 6-Cl | H | H | CH₃ | CH₃ | 4-CON(CH₃)₂ | CH |
| (220) | 6-Cl | H | H | CH₃ | CH₃ | 4-CON(CH₃)C₂H₅ | CH |
| (221) | 6-Cl | H | H | CH₃ | CH₃ | 4-CON(C₃H₇(n))₂ | CH |
| (222) | 6-Cl | H | H | CH₃ | CH₃ | 4-CONHC₂H₅ | CH |
| (223) | 6-Cl | H | H | CH₃ | CH₃ | 4-CONHC₃H₇(n) | CH |
| (224) | 6-Cl | H | H | CH₃ | CH₃ | 4-CONHC₃H₇(iso) | CH |
| (225) | 6-Cl | H | H | CH₃ | CH₃ | 4-CONHC₄H₉(n) | CH |
| (226) | 6-Cl | H | H | CH₃ | CH₃ | 4-CONHC₄H₉(t) | CH |
| (227) | 6-Cl | H | H | CH₃ | CH₃ | 4-CONHCH₂CH₂Cl | CH |

TABLE 1-continued

| Compound No. | R¹ | R² | R³ | R⁴ | R⁵ | R⁶ | X |
|---|---|---|---|---|---|---|---|
| (228) | 6-Cl | H | H | CH₃ | CH₃ | 4-CONH-(2-CH₃-phenyl) | CH |
| (229) | 6-Cl | H | H | CH₃ | CH₃ | 4-CONH-(3-CH₃-phenyl) | CH |
| (230) | 6-Cl | H | H | CH₃ | CH₃ | 4-CONH-(4-CH₃-phenyl) | CH |
| (231) | 6-Cl | H | H | CH₃ | CH₃ | 4-CONH-(2-Cl-phenyl) | CH |
| (232) | 6-Cl | H | H | CH₃ | CH₃ | 4-CONH-(3-F-phenyl) | CH |
| (233) | 6-Cl | H | H | CH₃ | CH₃ | 4-CONH-(4-Br-phenyl) | CH |
| (234) | 6-Cl | H | H | CH₃ | CH₃ | 4-CONHCH₂Ph | CH |
| (235) | 6-Cl | H | H | CH₃ | CH₃ | 4-CONHN(CH₃)₂ | CH |
| (236) | 6-F | H | H | CH₃ | CH₃ | 4-COOCH₂CF₃ | CH |
| (237) | 6-F | H | H | CH₃ | CH₃ | 4-COOCH₂CH₂Cl | CH |
| (238) | 6-F | H | H | CH₃ | CH₃ | 4-COOCH₂CH₂F | CH |
| (239) | 6-F | H | H | CH₃ | CH₃ | 4-COOCH₂CH₂Br | CH |
| (240) | 6-F | H | H | CH₃ | CH₃ | 4-COOCH₂CHF₂ | CH |
| (241) | 6-F | H | H | CH₃ | CH₃ | 4-COOCH₂CHCl₂ | CH |
| (242) | 6-F | H | H | CH₃ | CH₃ | 4-COOCH₂CH=CH₂ | CH |
| (243) | 6-F | H | H | CH₃ | CH₃ | 4-COOCH₂C≡CH | CH |
| (244) | 6-F | H | H | CH₃ | CH₃ | 4-COOCH₂CH=CHCl | CH |
| (245) | 6-F | H | H | CH₃ | CH₃ | 4-COOCH₂CH=CCl₂ | CH |
| (246) | 6-F | H | H | CH₃ | CH₃ | 4-COOCH₂CCl=CH₂ | CH |
| (247) | 6-F | H | H | CH₃ | CH₃ | 4-COOCH₂CH=CHF | CH |
| (248) | 6-F | H | H | CH₃ | CH₃ | 4-COOCH₂CH=CF₂ | CH |
| (249) | 6-F | H | H | CH₃ | CH₃ | 4-COOCH₂CF=CH₂ | CH |
| (250) | 6-F | H | H | CH₃ | CH₃ | 4-COOC₃H₇(iso) | CH |
| (251) | 6-F | H | H | CH₃ | CH₃ | 4-COOCH₂CH=CH(CH₃) | CH |
| (252) | 6-F | H | H | CH₃ | CH₃ | 4-COOCH(CH₃)=CH₂ | CH |
| (253) | 6-F | H | H | CH₃ | CH₃ | 4-COOC₄H₉(iso) | CH |
| (254) | 6-F | H | H | CH₃ | CH₃ | 4-COOC₄H₉(sec) | CH |
| (255) | 6-F | H | H | CH₃ | CH₃ | 4-COOC₄H₇(cyclo) | CH |

TABLE 1-continued

| Compound No. | R¹ | R² | R³ | R⁴ | R⁵ | R⁶ | X |
|---|---|---|---|---|---|---|---|
| (256) | 6-F | H | H | $CH_3$ | $CH_3$ | 4-COOC$_3$H$_5$(cyclo) | CH |
| (257) | 6-F | H | H | $CH_3$ | $CH_3$ | 4-COOCH(CH$_3$)C≡CH | CH |
| (258) | 6-F | H | H | $CH_3$ | $CH_3$ | 4-COOC$_4$H$_9$(t) | CH |
| (259) | 6-F | H | H | $CH_3$ | $CH_3$ | 4-COOCH(C$_2$H$_5$)$_2$ | CH |
| (260) | 6-F | H | H | $CH_3$ | $CH_3$ | 4-COOC$_5$H$_{11}$(n) | CH |
| (261) | 6-F | H | H | $CH_3$ | $CH_3$ | 4-COOCH$_2$CH=C(CH$_3$)$_2$ | CH |
| (262) | 6-F | H | H | $CH_3$ | $CH_3$ | 4-COOC(CH$_3$)$_2$CH=CH$_2$ | CH |
| (263) | 6-F | H | H | $CH_3$ | $CH_3$ | 4-COOC$_5$H$_9$(cyclo) | CH |
| (264) | 6-F | H | H | $CH_3$ | $CH_3$ | 4-COOCH(CH$_3$)C$_4$H$_9$ | CH |
| (265) | 6-F | H | H | $CH_3$ | $CH_3$ | 4-COOC$_7$H$_{15}$(n) | CH |
| (266) | 6-F | H | H | $CH_3$ | $CH_3$ | 4-COOCH$_2$CH$_2$OCH$_3$ | CH |
| (267) | 6-F | H | H | $CH_3$ | $CH_3$ | 4-COOCH$_2$CH$_2$OC$_2$H$_5$ | CH |
| (268) | 6-F | H | H | $CH_3$ | $CH_3$ | 4-COO-(2-Cl-phenyl) | CH |
| (269) | 6-F | H | H | $CH_3$ | $CH_3$ | 4-COO-(3-Cl-phenyl) | CH |
| (270) | 6-F | H | H | $CH_3$ | $CH_3$ | 4-COO-(4-Cl-phenyl) | CH |
| (271) | 6-F | H | H | $CH_3$ | $CH_3$ | 4-COO-(2-F-phenyl) | CH |
| (272) | 6-F | H | H | $CH_3$ | $CH_3$ | 4-COO-(3-F-phenyl) | CH |
| (273) | 6-F | H | H | $CH_3$ | $CH_3$ | 4-COO-(4-F-phenyl) | CH |
| (274) | 6-F | H | H | $CH_3$ | $CH_3$ | 4-COO-(2-CO$_2$C$_2$H$_5$-phenyl) | CH |
| (275) | 6-F | H | H | $CH_3$ | $CH_3$ | 4-COOCH$_2$Ph | CH |

TABLE 1-continued

| Compound No. | R¹ | R² | R³ | R⁴ | R⁵ | R⁶ | X |
|---|---|---|---|---|---|---|---|
| (276) | 6-F | H | H | $CH_3$ | $CH_3$ | 4-COOCH₂-(2-Cl-phenyl) | CH |
| (277) | 6-F | H | H | $CH_3$ | $CH_3$ | 4-COOCH₂-(3-CH₃-phenyl) | CH |
| (278) | 6-F | H | H | $CH_3$ | $CH_3$ | 4-COOCH₂-(2-thienyl) | CH |
| (279) | 6-F | H | H | $CH_3$ | $CH_3$ | 4-COOCH₂-(3-furyl) | CH |
| (280) | 6-F | H | H | $CH_3$ | $CH_3$ | 4-COOCH₂-(2-furyl) | CH |
| (281) | 6-F | H | H | $CH_3$ | $CH_3$ | 4-COO-cyclohexyl | CH |
| (282) | 6-F | H | H | $CH_3$ | $CH_3$ | 4-COO-cyclopentyl | CH |
| (283) | 6-F | H | H | $CH_3$ | $CH_3$ | 4-COOCH₂CH₂N(CH₃)₂ | CH |
| (284) | 6-F | H | H | $CH_3$ | $CH_3$ | 4-CN | CH |
| (285) | 6-F | H | H | $CH_3$ | $CH_3$ | 4-NH₂ | CH |
| (286) | 6-F | H | H | $CH_3$ | $CH_3$ | 4-NHCO₂CH₃ | CH |
| (287) | 6-F | H | H | $CH_3$ | $CH_3$ | 4-COSCH₃ | CH |
| (288) | 6-F | H | H | $CH_3$ | $CH_3$ | 4-COSC₂H₅ | CH |
| (289) | 6-F | H | H | $CH_3$ | $CH_3$ | 4-COSCH₂CH=CH₂ | CH |
| (290) | 6-F | H | H | $CH_3$ | $CH_3$ | 4-COSCH₂CH₂Cl | CH |
| (291) | 6-F | H | H | $CH_3$ | $CH_3$ | 4-COSCH₂CH₂OCH₃ | CH |
| (292) | 6-F | H | H | $CH_3$ | $CH_3$ | 4-COSC₃H₇(n) | CH |
| (293) | 6-F | H | H | $CH_3$ | $CH_3$ | 4-COSC₃H₇(iso) | CH |
| (294) | 6-F | H | H | $CH_3$ | $CH_3$ | 4-COSC₄H₉(n) | CH |
| (295) | 6-F | H | H | $CH_3$ | $CH_3$ | 4-CON(CH₃)₂ | CH |
| (296) | 6-F | H | H | $CH_3$ | $CH_3$ | 4-CON(CH₃)C₂H₅ | CH |
| (297) | 6-F | H | H | $CH_3$ | $CH_3$ | 4-CON(C₂H₅)₂ | CH |
| (298) | 6-F | H | H | $CH_3$ | $CH_3$ | 4-CON(C₃H₇(n))₂ | CH |
| (299) | 6-F | H | H | $CH_3$ | $CH_3$ | 4-COON=C(CH₃)₂ | CH |
| (300) | 6-F | H | H | $CH_3$ | $CH_3$ | 4-CONH₂ | CH |
| (301) | 6-F | H | H | $CH_3$ | $CH_3$ | 4-CONHCH₃ | CH |
| (302) | 6-F | H | H | $CH_3$ | $CH_3$ | 4-CONHC₂H₅ | CH |
| (303) | 6-F | H | H | $CH_3$ | $CH_3$ | 4-CONHC₃H₇(n) | CH |

TABLE 1-continued

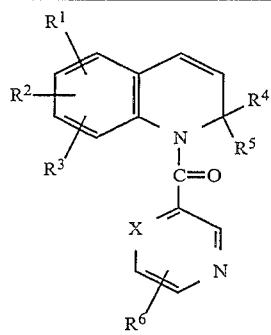

| Compound No. | R¹ | R² | R³ | R⁴ | R⁵ | R⁶ | X |
|---|---|---|---|---|---|---|---|
| (304) | 6-F | H | H | CH₃ | CH₃ | 4-CONHC₃H₇(iso) | CH |
| (305) | 6-F | H | H | CH₃ | CH₃ | 4-CONHC₄H₉(n) | CH |
| (306) | 6-F | H | H | CH₃ | CH₃ | 4-CONHC₄H₉(t) | CH |
| (307) | 6-F | H | H | CH₃ | CH₃ | 4-CONHCH₂CH₂Cl | CH |
| (308) | 6-F | H | H | CH₃ | CH₃ | 4-CONHCH₂CH=CH₂ | CH |
| (309) | 6-F | H | H | CH₃ | CH₃ | 4-CONHCH₂C≡CH | CH |
| (310) | 6-F | H | H | CH₃ | CH₃ | 4-CONHPh | CH |
| (311) | 6-F | H | H | CH₃ | CH₃ | 4-CONH-(2-CH₃-phenyl) | CH |
| (312) | 6-F | H | H | CH₃ | CH₃ | 4-CONH-(3-CH₃-phenyl) | CH |
| (313) | 6-F | H | H | CH₃ | CH₃ | 4-CONH-(4-CH₃-phenyl) | CH |
| (314) | 6-F | H | H | CH₃ | CH₃ | 4-CONH-(2-Cl-phenyl) | CH |
| (315) | 6-F | H | H | CH₃ | CH₃ | 4-CONH-(3-F-phenyl) | CH |
| (316) | 6-F | H | H | CH₃ | CH₃ | 4-CONH-(4-Br-phenyl) | CH |
| (317) | 6-F | H | H | CH₃ | CH₃ | 4-CONHCH₂Ph | CH |
| (318) | 6-F | H | H | CH₃ | CH₃ | 4-CONHNH₂ | CH |
| (319) | 6-F | H | H | CH₃ | CH₃ | 4-CONHN(CH₃)₂ | CH |
| (320) | 6-Br | H | H | CH₃ | CH₃ | 4-COOH | CH |
| (321) | 6-Br | H | H | CH₃ | CH₃ | 4-COOC₂H₅ | CH |
| (322) | 6-Br | H | H | CH₃ | CH₃ | 4-COOCH₂CF₃ | CH |
| (323) | 6-Br | H | H | CH₃ | CH₃ | 4-COOCH₂CH₂Cl | CH |
| (324) | 6-Br | H | H | CH₃ | CH₃ | 4-COOCH₂CH₂F | CH |
| (325) | 6-Br | H | H | CH₃ | CH₃ | 4-COOCH₂CH₂Br | CH |
| (326) | 6-Br | H | H | CH₃ | CH₃ | 4-COOCH₂CHF₂ | CH |
| (327) | 6-Br | H | H | CH₃ | CH₃ | 4-COOCH₂CHCl₂ | CH |
| (328) | 6-Br | H | H | CH₃ | CH₃ | 4-COOC₃H₇(n) | CH |
| (329) | 6-Br | H | H | CH₃ | CH₃ | 4-COOCH₂CH=CH₂ | CH |
| (330) | 6-Br | H | H | CH₃ | CH₃ | 4-COOCH₂C≡CH | CH |
| (331) | 6-Br | H | H | CH₃ | CH₃ | 4-COOCH₂CH=CHCl | CH |

TABLE 1-continued

| Compound No. | R¹ | R² | R³ | R⁴ | R⁵ | R⁶ | X |
|---|---|---|---|---|---|---|---|
| (332) | 6-Br | H | H | CH₃ | CH₃ | 4-COOCH₂CH=CCl₂ | CH |
| (333) | 6-Br | H | H | CH₃ | CH₃ | 4-COOCH₂CCl=CH₂ | CH |
| (334) | 6-Br | H | H | CH₃ | CH₃ | 4-COOCH₂CH=CHF | CH |
| (335) | 6-Br | H | H | CH₃ | CH₃ | 4-COOCH₂CH=CF₂ | CH |
| (336) | 6-Br | H | H | CH₃ | CH₃ | 4-COOCH₂CF=CH₂ | CH |
| (337) | 6-Br | H | H | CH₃ | CH₃ | 4-COOCH₂CH=CH(CH₃) | CH |
| (338) | 6-Br | H | H | CH₃ | CH₃ | 4-COOCH(CH₃)=CH₂ | CH |
| (339) | 6-Br | H | H | CH₃ | CH₃ | 4-COOC₄H₉(n) | CH |
| (340) | 6-Br | H | H | CH₃ | CH₃ | 4-COOC₄H₉(iso) | CH |
| (341) | 6-Br | H | H | CH₃ | CH₃ | 4-COOC₄H₉(sec) | CH |
| (342) | 6-Br | H | H | CH₃ | CH₃ | 4-COOC₄H₇(cyclo) | CH |
| (343) | 6-Br | H | H | CH₃ | CH₃ | 4-COOC₃H₅(cyclo) | CH |
| (344) | 6-Br | H | H | CH₃ | CH₃ | 4-COOCH(CH₃)C≡CH | CH |
| (345) | 6-Br | H | H | CH₃ | CH₃ | 4-COOC₄H₉(t) | CH |
| (346) | 6-Br | H | H | CH₃ | CH₃ | 4-COOCH(C₂H₅)₂ | CH |
| (347) | 6-Br | H | H | CH₃ | CH₃ | 4-COOC₅H₁₁(n) | CH |
| (348) | 6-Br | H | H | CH₃ | CH₃ | 4-COOCH₂CH=C(CH₃)₂ | CH |
| (349) | 6-Br | H | H | CH₃ | CH₃ | 4-COOC(CH₃)₂CH=CH₂ | CH |
| (350) | 6-Br | H | H | CH₃ | CH₃ | 4-COOC₅H₉(cyclo) | CH |
| (351) | 6-Br | H | H | CH₃ | CH₃ | 4-COOC₆H₁₃(n) | CH |
| (352) | 6-Br | H | H | CH₃ | CH₃ | 4-COOCH(CH₃)C₄H₉ | CH |
| (353) | 6-Br | H | H | CH₃ | CH₃ | 4-COOC₆H₁₁(cyclo) | CH |
| (354) | 6-Br | H | H | CH₃ | CH₃ | 4-COOC₇H₁₅(n) | CH |
| (355) | 6-Br | H | H | CH₃ | CH₃ | 4-COOCH₂CH₂OCH₃ | CH |
| (356) | 6-Br | H | H | CH₃ | CH₃ | 4-COOCH₂CH₂OC₂H₅ | CH |
| (357) | 6-Br | H | H | CH₃ | CH₃ | 4-COOPh | CH |
| (358) | 6-Br | H | H | CH₃ | CH₃ | 4-COO-(2-Cl-phenyl) | CH |
| (359) | 6-Br | H | H | CH₃ | CH₃ | 4-COO-(3-Cl-phenyl) | CH |
| (360) | 6-Br | H | H | CH₃ | CH₃ | 4-COO-(4-Cl-phenyl) | CH |
| (361) | 6-Br | H | H | CH₃ | CH₃ | 4-COO-(2-F-phenyl) | CH |
| (362) | 6-Br | H | H | CH₃ | CH₃ | 4-COO-(3-F-phenyl) | CH |

TABLE 1-continued

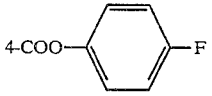

| Compound No. | R¹ | R² | R³ | R⁴ | R⁵ | R⁶ | X |
|---|---|---|---|---|---|---|---|
| (363) | 6-Br | H | H | CH₃ | CH₃ | 4-COO—⟨C₆H₄⟩—F | CH |
| (364) | 6-Br | H | H | CH₃ | CH₃ | 4-COO—⟨C₆H₄⟩—CO₂C₂H₅ | CH |
| (365) | 6-Br | H | H | CH₃ | CH₃ | 4-COOCH₂Ph | CH |
| (366) | 6-Br | H | H | CH₃ | CH₃ | 4-COOCH₂—⟨C₆H₄⟩—Cl | CH |
| (367) | 6-Br | H | H | CH₃ | CH₃ | 4-COOCH₂—⟨C₆H₄⟩—CH₃ | CH |
| (368) | 6-Br | H | H | CH₃ | CH₃ | 4-COOCH₂-(2-thienyl) | CH |
| (369) | 6-Br | H | H | CH₃ | CH₃ | 4-COOCH₂-(3-furyl) | CH |
| (370) | 6-Br | H | H | CH₃ | CH₃ | 4-COOCH₂-(2-furyl) | CH |
| (371) | 6-Br | H | H | CH₃ | CH₃ | 4-COO-cyclohexyl | CH |
| (372) | 6-Br | H | H | CH₃ | CH₃ | 4-COO-cyclopentyl | CH |
| (373) | 6-Br | H | H | CH₃ | CH₃ | 4-COOCH₂CH₂N(CH₃)₂ | CH |
| (374) | 6-Br | H | H | CH₃ | CH₃ | 4-CN | CH |
| (375) | 6-Br | H | H | CH₃ | CH₃ | 4-NH₂ | CH |
| (376) | 6-Br | H | H | CH₃ | CH₃ | 4-NHCO₂CH₃ | CH |
| (377) | 6-Br | H | H | CH₃ | CH₃ | 4-COSCH₃ | CH |
| (378) | 6-Br | H | H | CH₃ | CH₃ | 4-COSC₂H₅ | CH |

TABLE 1-continued

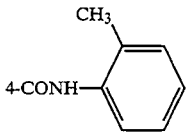

| Compound No. | R¹ | R² | R³ | R⁴ | R⁵ | R⁶ | X |
|---|---|---|---|---|---|---|---|
| (379) | 6-Br | H | H | $CH_3$ | $CH_3$ | 4-$COSCH_2CH=CH_2$ | CH |
| (380) | 6-Br | H | H | $CH_3$ | $CH_3$ | 4-$COSCH_2CH_2Cl$ | CH |
| (381) | 6-Br | H | H | $CH_3$ | $CH_3$ | 4-$COSCH_2CH_2OCH_3$ | CH |
| (382) | 6-Br | H | H | $CH_3$ | $CH_3$ | 4-$COSC_3H_7(n)$ | CH |
| (383) | 6-Br | H | H | $CH_3$ | $CH_3$ | 4-$COSC_3H_7(iso)$ | CH |
| (384) | 6-Br | H | H | $CH_3$ | $CH_3$ | 4-$COSC_4H_9(n)$ | CH |
| (385) | 6-Br | H | H | $CH_3$ | $CH_3$ | 4-$CON(CH_3)_2$ | CH |
| (386) | 6-Br | H | H | $CH_3$ | $CH_3$ | 4-$CON(CH_3)C_2H_5$ | CH |
| (387) | 6-Br | H | H | $CH_3$ | $CH_3$ | 4-$CON(C_2H_5)_2$ | CH |
| (388) | 6-Br | H | H | $CH_3$ | $CH_3$ | 4-$CON(C_3H_7(n))_2$ | CH |
| (389) | 6-Br | H | H | $CH_3$ | $CH_3$ | 4-$COON=C(CH_3)_2$ | CH |
| (390) | 6-Br | H | H | $CH_3$ | $CH_3$ | 4-$CONH_2$ | CH |
| (391) | 6-Br | H | H | $CH_3$ | $CH_3$ | 4-$CONHCH_3$ | CH |
| (392) | 6-Br | H | H | $CH_3$ | $CH_3$ | 4-$CONHC_2H_5$ | CH |
| (393) | 6-Br | H | H | $CH_3$ | $CH_3$ | 4-$CONHC_3H_7(n)$ | CH |
| (394) | 6-Br | H | H | $CH_3$ | $CH_3$ | 4-$CONHC_3H_7(iso)$ | CH |
| (395) | 6-Br | H | H | $CH_3$ | $CH_3$ | 4-$CONHC_4H_9(n)$ | CH |
| (396) | 6-Br | H | H | $CH_3$ | $CH_3$ | 4-$CONHC_4H_9(t)$ | CH |
| (397) | 6-Br | H | H | $CH_3$ | $CH_3$ | 4-$CONHCH_2CH_2Cl$ | CH |
| (398) | 6-Br | H | H | $CH_3$ | $CH_3$ | 4-$CONHCH_2CH=CH_2$ | CH |
| (399) | 6-Br | H | H | $CH_3$ | $CH_3$ | 4-$CONHCH_2C\equiv CH$ | CH |
| (400) | 6-Br | H | H | $CH_3$ | $CH_3$ | 4-CONHPh | CH |
| (401) | 6-Br | H | H | $CH_3$ | $CH_3$ | 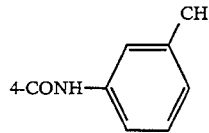 | CH |
| (402) | 6-Br | H | H | $CH_3$ | $CH_3$ | 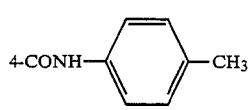 | CH |
| (403) | 6-Br | H | H | $CH_3$ | $CH_3$ | 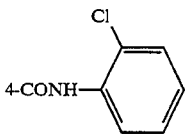 | CH |
| (404) | 6-Br | H | H | $CH_3$ | $CH_3$ | 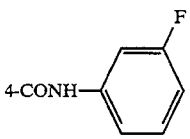 | CH |
| (405) | 6-Br | H | H | $CH_3$ | $CH_3$ | 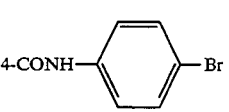 | CH |
| (406) | 6-Br | H | H | $CH_3$ | $CH_3$ | 4-CONH—⟨⟩—Br | CH |

TABLE 1-continued

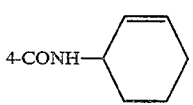

| Compound No. | R¹ | R² | R³ | R⁴ | R⁵ | R⁶ | X |
|---|---|---|---|---|---|---|---|
| (407) | 6-Br | H | H | CH₃ | CH₃ | 4-CONHCH₂Ph | CH |
| (408) | 6-Br | H | H | CH₃ | CH₃ | 4-CONHNH₂ | CH |
| (409) | 6-Br | H | H | CH₃ | CH₃ | 4-CONHN(CH₃)₂ | CH |
| (410) | H | H | H | CH₃ | CH₃ | 4-COOH | CH |
| (411) | H | H | H | CH₃ | CH₃ | 4-COOC₃H₇(n) | CH |
| (412) | H | H | H | CH₃ | CH₃ | 4-COOC₄H₉(n) | CH |
| (413) | H | H | H | CH₃ | CH₃ | 4-COOC₄H₉(t) | CH |
| (414) | H | H | H | CH₃ | CH₃ | 4-COSCH₃ | CH |
| (415) | H | H | H | CH₃ | CH₃ | 4-CONHCH₃ | CH |
| (416) | H | H | H | CH₃ | CH₃ | 4-CN | CH |
| (417) | H | H | H | CH₃ | CH₃ | 4-NH₂ | CH |
| (418) | H | H | H | CH₃ | CH₃ | 4-NH(CH₃) | CH |
| (419) | 6-OCH₃ | H | H | CH₃ | CH₃ | 4-COOH | CH |
| (420) | 6-OCH₃ | H | H | CH₃ | CH₃ | 4-CN | CH |
| (421) | 6-OCH₃ | H | H | CH₃ | CH₃ | 4-NH₂ | CH |
| (422) | 6-SCH₃ | H | H | CH₃ | CH₃ | 4-CO₂CH₃ | CH |
| (423) | 6-SCH₃ | H | H | CH₃ | CH₃ | 4-Cl | CH |
| (424) | 6-SCH₃ | H | H | CH₃ | CH₃ | 4-CN | CH |
| (425) | 6-SCH₃ | H | H | CH₃ | CH₃ | 4-NH₂ | CH |
| (426) | 6-SCH₃ | H | H | CH₃ | CH₃ | 4-CONHCH₃ | CH |
| (427) | 6-Ph | H | H | CH₃ | CH₃ | 4-COOH | CH |
| (428) | 6-Ph | H | H | CH₃ | CH₃ | 4-COOC₃H₇(n) | CH |
| (429) | H | H | H | —(CH₂)₂— | | H | CH |
| (430) | 6-Cl | H | H | —(CH₂)₂— | | H | CH |
| (431) | 6-F | H | H | —(CH₂)₂— | | H | CH |
| (432) | H | H | H | —(CH₂)₂— | | 4-CO₂CH₃ | CH |
| (433) | 6-Cl | H | H | —(CH₂)₂— | | 4-CO₂C₃H₇(i) | CH |
| (434) | 6-F | H | H | —(CH₂)₂— | | 4-CONHCH₃ | CH |
| (435) | 6-Br | H | H | —(CH₂)₂— | | 4-CN | CH |
| (436) | H | H | H | —(CH₂)₅— | | 4-CO₂CH₃ | CH |
| (437) | 6-Cl | H | H | —(CH₂)₅— | | 4-CONHCH₃ | CH |
| (438) | 6-Ph | H | H | —(CH₂)₅— | | H | CH |
| (439) | 6-Cl | H | H | CH₃ | CH₃ | 4-CO₂CH₂CHClC≡CH | CH |
| (440) | 6-F | H | H | CH₃ | CH₃ | 4-CO₂CH(CH₂Cl)C≡CCH₃ | CH |
| (441) | 6-Cl | H | H | CH₃ | CH₃ | 4-CO₂CH₂OC₂H₅ | CH |
| (442) | H | H | H | CH₃ | CH₃ | 4-CO₂CH₂CH(CH₃)CH₂OC₃H₇ | CH |
| (443) | 6-Cl | H | H | CH₃ | CH₃ | 4-CO₂CH₂CH(CH₃)CHNHCH₃ | CH |
| (444) | H | H | H | CH₃ | CH₃ | 4-CO₂CH₂CH₂N(C₂H₅)₂ | CH |
| (445) | 6-Cl | H | H | CH₃ | CH₃ | 4-CO₂N(CH₃)₂ | CH |
| (446) | 6-Cl | H | H | CH₃ | CH₃ | 4-CO₂NHC₄H₉(n) | CH |
| (447) | H | H | H | CH₃ | CH₃ | 4-CONHCH₂CClC=CH₂ | CH |
| (448) | 6-Cl | H | H | CH₃ | CH₃ | 4-CONHCH₂CH₂CH=CCl₂ | CH |
| (449) | H | H | H | CH₃ | CH₃ | 4-CONHCH₂CHClCH₂C≡CH | CH |
| (450) | 6-Cl | H | H | CH₃ | CH₃ | 4-CONHCH₂C≡CCH₂CHF₂ | CH |
| (451) | H | H | H | CH₃ | CH₃ | 4-CONHC₃H₅(cyclo) | CH |
| (452) | 6-Cl | H | H | CH₃ | CH₃ | 4-CONHC₆H₁₁(cyclo) | CH |
| (453) | H | H | H | CH₃ | CH₃ | 4-CONH—cyclohexenyl | CH |
| (454) | 6-Cl | H | H | CH₃ | CH₃ | 4-CONH—cyclopentenyl | CH |
| (455) | 6-N(CH₃)₂ | H | H | CH₃ | CH₃ | 4-Br | CH |
| (456) | 6-N(CH₃)₂ | H | H | CH₃ | CH₃ | 4-Cl | CH |
| (457) | 6-NHC₄H₉(n) | H | H | CH₃ | CH₃ | H | CH |
| (458) | 6-Ph | H | H | CH₃ | CH₃ | 4-CN | CH |

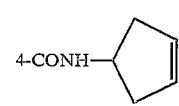

TABLE 1-continued

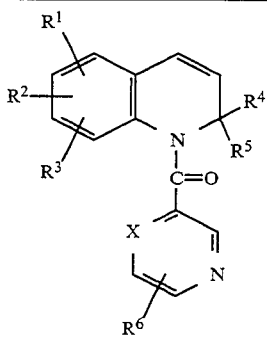

| Compound No. | R¹ | R² | R³ | R⁴ | R⁵ | R⁶ | X |
|---|---|---|---|---|---|---|---|
| (459) | 6-Ph | H | H | CH₃ | CH₃ | 4-NH₂ | CH |

Table 2 illustrates physical properties of some compounds in Table 1.

TABLE 2

| Compound No. | Physical properties ($n_D$, melting point) |
|---|---|
| (1) | 127.8° C. (decomposition) |
| (2) | 120.9° C. (decomposition) |
| (3) | 114.7° C. (decomposition) |
| (4) | 41.4° C. |
| (5) | resinous |
| (6) | 122.6° C. |
| (7) | $n_D^{26}$ 1.5948 |
| (8) | 130.6° C. |
| (9) | 132.6° C. |
| (10) | 114.7° C. |
| (11) | 108.8° C. |
| (12) | 92.5° C. |
| (13) | 87.8° C. |
| (14) | $n_D^{24}$ 1.6091 |
| (15) | $n_D^{24}$ 1.5672 |
| (16) | $n_D^{24}$ 1.5571 |
| (17) | $n_D^{24}$ 1.5453 |
| (18) | $n_D^{24}$ 1.5872 |
| (19) | $n_D^{24}$ 1.5862 |
| (20) | $n_D^{24}$ 1.6015 |
| (21) | 61.3° C. |
| (22) | 107.1° C. |
| (23) | $n_D^{24}$ 1.4958 |
| (24) | $n_D^{24}$ 1.5995 |
| (25) | $n_D^{24}$ 1.6002 |
| (26) | $n_D^{24}$ 1.5821 |
| (27) | $n_D^{24}$ 1.5338 |
| (28) | resinous |
| (29) | resinous |
| (30) | 166.1° C. (decomposition) |
| (31) | 93.5° C. |
| (32) | 118.8° C. |
| (33) | 106.3° C. |
| (34) | resinous |
| (35) | 68.8° C. |
| (36) | 169.6° C. (decomposition) |
| (37) | 147.5° C. |
| (38) | 94.1° C. |
| (39) | 95.8° C. |
| (40) | resinous |
| (41) | 115.3° C. |
| (42) | 127.9° C. |
| (43) | 108.7° C. |
| (44) | 116.1° C. |
| (45) | 128.8° C. |
| (46) | 119.8° C. |
| (47) | 82.9° C. |
| (48) | 119.1° C. (decomposition) |
| (49) | 160.8° C. |
| (50) | resinous |
| (51) | resinous |
| (52) | 74.2° C. |
| (53) | 102.7° C. |
| (54) | 108.1° C. |

TABLE 2-continued

| Compound No. | Physical properties ($n_D$, melting point) |
|---|---|
| (55) | 113.4° C. |
| (56) | 130.2° C. |
| (57) | 120.7° C. |
| (58) | 146.4° C. |
| (59) | 114.7° C. |
| (60) | 69.0° C. |
| (61) | resinous |
| (62) | 94.0° C. |
| (63) | 105.6° C. |
| (64) | 91.0° C. |
| (65) | 114.4° C. |
| (66) | 101.1° C. |
| (67) | 116.1° C. |
| (68) | 111.7° C. (decomposition) |
| (69) | 106.1° C. |
| (70) | 226° C. (decomposition) |
| (71) | 148.7° C. (decomposition) |
| (72) | 88.3° C. |
| (73) | 166.1° C. |
| (74) | 154.8° C. |
| (75) | 194.5° C. |
| (76) | 128.5° C. |
| (77) | 207.8° C. (decomposition) |
| (78) | 153.2° C. |
| (79) | resinous |
| (80) | 200.7° C. (decomposition) |
| (81) | resinous |
| (82) | 125.9° C. |
| (83) | 200.6° C. (decomposition) |
| (84) | 145.1° C. |
| (85) | 137.7° C. (decomposition) |
| (86) | 83.7° C. (decomposition) |
| (87) | resinous |
| (88) | 114.5° C. (decomposition) |
| (89) | resinous |
| (90) | 148.7° C. (decomposition) |
| (91) | 137.4° C. |
| (92) | resinous |
| (93) | resinous |
| (94) | resinous |
| (95) | 82.5° C. (decomposition) |
| (96) | 90.6° C. |
| (97) | 154.2° C. (decomposition) |
| (98) | 175.3° C. |
| (99) | 142.9° C. (decomposition) |
| (100) | 127.7° C. (decomposition) |
| (101) | 99.6° C. (decomposition) |
| (102) | 75.8° C. |
| (103) | 61.1° C. |
| (104) | 160.8° C. (decomposition) |
| (105) | 157.2° C. (decomposition) |
| (106) | 157.6° C. |
| (107) | resinous |
| (108) | resinous |
| (109) | resinous |
| (110) | resinous |
| (111) | 109.4° C. |

TABLE 2-continued

| Compound No. | Physical properties (n_D, melting point) |
|---|---|
| (112) | 159.5° C. (decomposition) |
| (113) | resinous |
| (114) | resinous |
| (115) | resinous |
| (116) | resinous |
| (117) | 84.1° C. |

Formulation examples are shown below. In the examples, the present compound (I) is shown by Compound No. in Table 1, and parts are by weight.

FORMULATION EXAMPLE 1

Fifty parts of the present compound (1)–(117), 3 parts of calcium lignosulfonate, 2 parts of sodium lauryl sulfate and 45 parts of synthetic hydrated silicon dioxide are well mixed while being powdered to obtain a wettable powder.

FORMULATION EXAMPLE 2

Ten parts of the present compound (1)–(117), 14 parts of polyoxyethylene styrylphenyl ether, 6 parts of calcium dodecylbenzenesulfonate, 35 parts of xylene and 35 parts of cyclohexanone are well mixed to obtain an emulsifiable concentrate.

FORMULATION EXAMPLE 3

Two parts of the present compound (1)–(117), 2 parts of synthetic hydrated silicon dioxide, 2 parts of calcium lignosulfonate, 30 parts of bentonite and 64 parts of kaolin clay are well pulverized and mixed. The resulting mixture is well kneaded with water, granulated and dried to obtain a granule.

FORMULATION EXAMPLE 4

Twenty five parts of the present compound (1)–(4), (6), (8)–(13), (21)–(22), (30)–(33), (35)–(37), (38)–(39), (41)–(49), (52)–(61), (62)–(78), (80), (82)–(86), (88), (90)–(91), (95)–(106), (111)–(112) and (117), 50 parts of polyvinyl alcohol (10% aq.), 25 parts of water are mixed and wet-pulverized until the particle size decreases to 5 microns or less. Thus, a suspension formulation is obtained.

FORMULATION EXAMPLE 5

Forty parts of the polyvinyl alcohol (10% aq.) and 5 parts of the present compound (5), (7), (14)–(20), (23)–(29), (34), (40), (50)–(51), (79), (81), (87), (89), (92)–(94), (107)–(110) and (113)–(116) go into emulsified-dispersion until the particle size decreases to 10 microns or less and then 55 parts of water is added to obtain emulsifiable concentrates.

TABLE 3

| Compound symbol | Structural formula | Remarks |
|---|---|---|
| A | 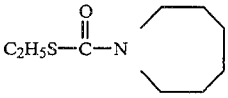 | molinate |
| B | Cl, NH₂, Cl, Cl, N, COOH (pyridine structure) | picloram |
| C | Cl–C₆H₃(Cl)–OCH₂COOH | 2,4-D |
| D | (C₂H₅)₂N–C(=O)–S–CH₂–C₆H₄–Cl | thiobencarb |

The herbicidal activity and phytotoxicity were evaluated in eleven stages, 0, 1, 2, 3, 4, 5, 6, 7, 8, 9 and 10 by comparing germination and growth of test plants with those untreated.

[0]: the states of germination and growth of test plants showed no difference.

[10]: test plants either completely died or germination/growth were totally inhibited.

TEST EXAMPLE 1

Soil Surface Treatment Test in Upland Field

Cylindrical plastic pots of 10 cm in diameter and 10 cm in depth were filled with upland field soil, and seeds of barnyardgrass were sowed in the pots and covered with soil. The test compounds were formulated into emulsifiable concentrates according to Formulation Example 2, and the prescribed amount of each emulsifiable concentrate was diluted with water at a spray volume of 1000 liters/hectare and uniformly applied onto the whole soil surface by means of a sprayer. After application, the test plants were cultivated for 19 days in a greenhouse, and the herbicidal activity was examined. The results are shown in Table 4.

TABLE 4

| Test compound | Dosage rate of active ingredient (g/ha) | Herbicidal activity barnyardgrass |
|---|---|---|
| (1) | 2000 | 9 |
| (2) | 2000 | 10 |
| (10) | 2000 | 8 |
| (11) | 2000 | 9 |
| (12) | 2000 | 7 |
| (14) | 2000 | 8 |
| (27) | 2000 | 7 |
| (28) | 2000 | 10 |
| (29) | 2000 | 9 |
| (31) | 500 | 10 |
| (32) | 2000 | 8 |
| (33) | 2000 | 8 |
| (34) | 500 | 8 |
| (37) | 2000 | 10 |
| (38) | 2000 | 9 |
| (40) | 2000 | 8 |
| (41) | 2000 | 10 |
| (42) | 2000 | 9 |
| (43) | 2000 | 10 |
| (44) | 2000 | 9 |
| (45) | 2000 | 9 |
| (49) | 500 | 8 |

TABLE 4-continued

| Test compound | Dosage rate of active ingredient (g/ha) | Herbicidal activity barnyardgrass |
|---|---|---|
| (64) | 2000 | 9 |
| (65) | 2000 | 8 |
| (69) | 2000 | 9 |
| (70) | 500 | 10 |
| (72) | 500 | 9 |
| (73) | 2000 | 9 |
| (74) | 2000 | 9 |
| (75) | 2000 | 10 |
| (76) | 2000 | 9 |
| (77) | 2000 | 8 |
| (78) | 500 | 9 |
| (81) | 500 | 9 |
| (83) | 500 | 9 |
| (84) | 500 | 8 |
| (85) | 500 | 8 |
| (86) | 500 | 10 |
| (87) | 500 | 9 |
| (88) | 500 | 9 |
| (90) | 500 | 9 |
| (91) | 2000 | 9 |
| (92) | 2000 | 9 |
| (93) | 2000 | 8 |
| (98) | 2000 | 8 |
| (99) | 2000 | 8 |
| (104) | 2000 | 8 |
| (105) | 500 | 10 |
| (106) | 500 | 10 |
| (107) | 2000 | 10 |
| (108) | 500 | 9 |
| (109) | 500 | 8 |
| (112) | 500 | 10 |
| (A) | 2000 | 0 |

TEST EXAMPLE 2

Soil Surface Treatment Test in Upland Field

Cylindrical plastic pots of 10 cm in diameter and 10 cm in depth were filled with upland field soil, and seeds of ivyleaf morningglory were sowed in the respective pots and covered with soil. The test compounds were formulated into emulsifiable concentrates according to Formulation Example 2, and the prescribed amount of each emulsifiable concentrate was diluted with water at a spray volume of 1000 liters/hectare and uniformly applied onto the whole soil surface by means of a sprayer. After application, the test plants were cultivated for 19 days in a greenhouse, and the herbicidal activity was examined. The results are shown in Table 5.

TABLE 5

| Test compound | Dosage rate of active ingredient (g/ha) | Herbicidal activity Ivyleaf morningglory |
|---|---|---|
| (46) | 2000 | 9 |
| (47) | 2000 | 9 |
| (48) | 500 | 8 |

TEST EXAMPLE 3

Foliar Treatment Test in Upland Field

Cylindrical plastic pots of 10 cm in diameter and 10 cm in depth were filled with upland field soil, and the seeds of barnyardgrass sowed in the pot and cultivated for 7 days in a greenhouse.

Thereafter, the test compounds were formulated into emulsifiable concentrates according to Formulation Example 2 and the prescribed amount of each emulsifiable concentrate was diluted with a spreading agent-containing water at a spray volume of 1000 liters/hectare and uniformly applied from above onto the whole foliar portion of the test plants by means of a sprayer. After application, the test plants were cultivated for 19 days in a greenhouse, and the herbicidal activity was examined.

The results are shown in Table 6.

TABLE 6

| Test compound | Dosage rate of active ingredient (g/ha) | Herbicidal activity barnyardgrass |
|---|---|---|
| (1) | 2000 | 8 |
| (2) | 2000 | 9 |
| (6) | 2000 | 8 |
| (7) | 2000 | 9 |
| (10) | 2000 | 10 |
| (11) | 2000 | 9 |
| (13) | 2000 | 9 |
| (15) | 2000 | 9 |
| (16) | 2000 | 9 |
| (27) | 8000 | 9 |
| (28) | 500 | 8 |
| (29) | 500 | 9 |
| (B) | 4000 | 4 |

TEST EXAMPLE 4

Foliar Treatment Test in Upland Field

Cylindrical plastic pots of 10 cm in diameter and 10 cm in depth were filled with upland field soil, and the seeds of test plants shown in Table 7 were sowed in the respective pots and cultivated for 7 days in a greenhouse.

Thereafter, the test compounds were formulated into emulsifiable concentrates according to Formulation Example 2 and the prescribed amount of each emulsifiable concentrate was diluted with a spreading agent-containing water at a spray volume of 1000 liters/hectare and uniformly applied from above onto the whole foliar portion of the test plants by means of a sprayer. After application, the test plants were cultivated for 19 days in a greenhouse, and the herbicidal activity was examined.

The results are shown in Table 7.

TABLE 7

| Test compound | Dosage rate of active ingredient (g/ha) | Herbicidal activity | | |
|---|---|---|---|---|
| | | Barnyardgrass | Ivyleaf morningglory | Velvetleaf |
| (31) | 2000 | 9 | 8 | 8 |
| (32) | 2000 | 7 | 7 | 8 |
| (33) | 500 | 7 | 8 | 7 |
| (34) | 2000 | 10 | 8 | 8 |
| (35) | 500 | 8 | 8 | 7 |
| (37) | 2000 | 9 | 8 | 8 |
| (38) | 2000 | 8 | 8 | 8 |
| (39) | 2000 | 8 | 7 | 7 |
| (42) | 2000 | 9 | 8 | 8 |
| (43) | 500 | 8 | 8 | 8 |
| (48) | 2000 | 8 | 7 | 8 |
| (49) | 2000 | 8 | 8 | 7 |
| (53) | 500 | 7 | 8 | 8 |
| (65) | 2000 | 7 | 8 | 7 |
| (68) | 2000 | 8 | 8 | 9 |
| (72) | 2000 | 10 | 10 | 7 |
| (75 | 2000 | 7 | 8 | 8 |
| (82) | 2000 | 9 | 8 | 7 |
| (83) | 2000 | 8 | 8 | 7 |
| (84) | 500 | 8 | 8 | 8 |
| (99) | 2000 | 7 | 8 | 8 |
| (106) | 500 | 8 | 8 | 7 |
| (107) | 2000 | 10 | 8 | 8 |
| (109) | 2000 | 10 | 8 | 8 |

TEST EXAMPLE 5

Foliar Treatment Test in Upland Field

Cylindrical plastic pots of 10 cm in diameter and 10 cm in depth were filled with upland field soil, and the seeds of ivyleaf morningglory were sowed in the respective pots and cultivated for 7 days in a greenhouse.

Thereafter, the test compounds were formulated into emulsifiable concentrates according to Formulation Example 2 and the prescribed amount of each emulsifiable concentrate was diluted with a spreading agent-containing water at a spray volume of 1000 liters/hectare and uniformly applied from above onto the whole foliar portion of the test plant by means of a sprayer. After application, the test plants were cultivated for 19 days in a greenhouse, and the herbicidal activity was examined. The results are shown in Table 8.

TABLE 8

| Test compound | Dosage rate of active ingredient (g/ha) | Herbicidal activity Ivyleaf morningglory |
|---|---|---|
| (30) | 500 | 8 |
| (36) | 2000 | 8 |
| (40) | 500 | 8 |
| (41) | 500 | 8 |
| (44) | 500 | 8 |
| (45) | 125 | 8 |
| (46) | 500 | 8 |
| (47) | 500 | 8 |
| (50) | 500 | 8 |
| (51) | 500 | 8 |
| (52) | 125 | 8 |
| (54) | 500 | 8 |
| (55) | 500 | 8 |
| (56) | 125 | 8 |
| (57) | 125 | 8 |
| (58) | 500 | 8 |
| (59) | 500 | 8 |
| (60) | 125 | 8 |
| (61) | 2000 | 8 |
| (62) | 500 | 7 |
| (63) | 500 | 7 |
| (64) | 500 | 8 |
| (66) | 500 | 7 |
| (67) | 500 | 7 |
| (69) | 500 | 8 |
| (70) | 125 | 8 |
| (71) | 2000 | 8 |
| (76) | 500 | 7 |
| (77) | 125 | 8 |
| (78) | 125 | 8 |
| (79) | 2000 | 8 |
| (80) | 2000 | 8 |
| (81) | 125 | 8 |
| (85) | 500 | 8 |
| (86) | 2000 | 8 |
| (88) | 500 | 8 |
| (90) | 500 | 8 |
| (91) | 500 | 7 |
| (92) | 2000 | 8 |
| (93) | 500 | 7 |
| (94) | 2000 | 8 |
| (95) | 500 | 8 |
| (96) | 500 | 7 |
| (100) | 500 | 8 |
| (101) | 500 | 7 |
| (102) | 2000 | 8 |
| (103) | 2000 | 8 |
| (105) | 500 | 8 |
| (108) | 500 | 8 |
| (110) | 2000 | 8 |
| (111) | 500 | 7 |
| (112) | 500 | 7 |
| (114) | 2000 | 8 |
| (116) | 125 | 7 |

TEST EXAMPLE 6

Flooding Treatment Test in Paddy Field

Cylindrical plastic pots of 9 cm in diameter and 11 cm in depth were filled with paddy field soil, and seeds of *Echinochola oryzicola* were sowed. After creating a state of paddy field by flooding, rice (at the 2-leaf stage) was transplanted and cultivated in a greenhouse. After 5 days, the test compounds were formulated into emulsifiable concentrates according to Formulation Example 2, and the prescribed amount of each emulsifiable concentrate was diluted with water and applied onto the water surface. After application, the test plants were cultivated for 19 days in a greenhouse, and the herbicidal activity and phytotoxicity were examined. The results are shown in Table 9.

TABLE 9

| Test compound | Dosage rate of active ingredient (g/ha) | Phytotoxicity Rice | Herbicidal activity E. oryzicola |
|---|---|---|---|
| (1) | 250 | 0 | 10 |
| (2) | 250 | 0 | 10 |
| (5) | 250 | 0 | 9 |
| (6) | 250 | 0 | 10 |
| (7) | 250 | 0 | 8 |
| (10) | 250 | 0 | 10 |
| (11) | 250 | 0 | 10 |
| (13) | 250 | 0 | 10 |
| (15) | 250 | 0 | 10 |
| (16) | 250 | 0 | 10 |
| (21) | 250 | 0 | 9 |
| (27) | 250 | 0 | 10 |
| (28) | 63 | 0 | 10 |
| (29) | 63 | 0 | 10 |
| (31) | 16 | 0 | 9 |
| (32) | 63 | 0 | 10 |
| (33) | 16 | 0 | 10 |
| (34) | 63 | 0 | 10 |
| (35) | 16 | 0 | 10 |
| (36) | 63 | 0 | 10 |
| (37) | 16 | 0 | 10 |
| (38) | 63 | 2 | 9 |
| (39) | 16 | 0 | 9 |
| (40) | 16 | 0 | 10 |
| (41) | 63 | 0 | 10 |
| (42) | 63 | 0 | 9 |
| (43) | 63 | 0 | 9 |
| (44) | 63 | 0 | 9 |
| (45) | 63 | 0 | 10 |
| (46) | 16 | 0 | 8 |
| (47) | 63 | 0 | 8 |
| (48) | 250 | 0 | 9 |
| (49) | 16 | 0 | 9 |
| (50) | 250 | 1 | 9 |
| (51) | 250 | 2 | 9 |
| (52) | 250 | 2 | 7 |
| (53) | 16 | 0 | 10 |
| (54) | 63 | 0 | 8 |
| (55) | 250 | 0 | 9 |
| (56) | 63 | 0 | 8 |
| (57) | 250 | 0 | 9 |
| (58) | 250 | 0 | 10 |
| (59) | 250 | 1 | 9 |
| (60) | 63 | 0 | 8 |
| (61) | 63 | 0 | 9 |
| (62) | 250 | 0 | 9 |
| (63) | 250 | 0 | 7 |
| (64) | 250 | 0 | 7 |
| (65) | 63 | 0 | 8 |
| (66) | 250 | 0 | 9 |
| (67) | 250 | 2 | 7 |
| (68) | 250 | 0 | 9 |
| (69) | 250 | 0 | 9 |
| (70) | 63 | 1 | 8 |
| (72) | 250 | 3 | 10 |
| (73) | 63 | 0 | 9 |
| (74) | 63 | 0 | 8 |

TABLE 9-continued

| Test compound | Dosage rate of active ingredient (g/ha) | Phytotoxicity Rice | Herbicidal activity E. oryzicola |
|---|---|---|---|
| (75) | 250 | 0 | 10 |
| (76) | 63 | 0 | 9 |
| (77) | 63 | 1 | 8 |
| (78) | 63 | 0 | 10 |
| (79) | 250 | 0 | 9 |
| (80) | 250 | 0 | 10 |
| (81) | 63 | 0 | 9 |
| (82) | 63 | 0 | 9 |
| (83) | 16 | 0 | 9 |
| (84) | 63 | 0 | 10 |
| (85) | 63 | 2 | 7 |
| (86) | 63 | 2 | 9 |
| (87) | 63 | 2 | 9 |
| (88) | 250 | 1 | 10 |
| (90) | 63 | 2 | 9 |
| (91) | 16 | 0 | 9 |
| (92) | 250 | 1 | 10 |
| (98) | 63 | 1 | 9 |
| (99) | 250 | 0 | 7 |
| (100) | 250 | 0 | 9 |
| (103) | 250 | 0 | 7 |
| (105) | 63 | 1 | 10 |
| (106) | 63 | 0 | 10 |
| (107) | 250 | 0 | 10 |
| (108) | 63 | 0 | 9 |
| (109) | 63 | 1 | 9 |
| (110) | 250 | 2 | 8 |
| (111) | 63 | 0 | 8 |
| (112) | 16 | 1 | 9 |
| (113) | 250 | 2 | 8 |

TEST EXAMPLE 7

Soil Treatment Test in Upland Field

Vats of 33×23 cm² in area and 11 cm in depth were filled with upland field soil, and the seeds of the test plant shown in Table 10 were sowed in the respective vats and covered with soil in a thickness of 1 to 2 cm. The test compounds were formulated into emulsifiable concentrates according to Formulation Example 2, and the prescribed amount of each emulsifiable concentrate was diluted with water at a spray volume of 1000 liters/hectare and uniformly applied onto the whole soil surface by means of a sprayer. After application, the test plants were cultivated for 18 days in a greenhouse, and the herbicidal activity and phytotoxicity were examined. The results are shown in Table 10.

TEST EXAMPLE 8

Soil Treatment Test in Upland Field

Vats of 25×18 cm² in area and 7 cm in depth were filled with upland field soil, and the seeds of the test plants shown in Table 11 were sowed in the respective vats. The test compounds were formulated into emulsifiable concentrates according to Formulation Example 2, and the prescribed amount of each emulsifiable concentrate was diluted with water at a spray volume of 1000 liters/hectare and uniformly applied onto the whole soil surface by means of a sprayer. After application, the test plants were cultivated for 18 days in a greenhouse, and the herbicidal activity and phytotoxicity were examined. The results are shown in Table 11.

TABLE 11

| Test compound | Dosage rate of active ingredient (g/ha) | Phyto-toxicity Corn | Herbicidal activity | | |
|---|---|---|---|---|---|
| | | | Giant foxtail | Barnyard-grass | Johnson-grass |
| (37) | 1000 | 0 | 8 | 7 | 8 |
| (42) | 1000 | 0 | 8 | 9 | — |
| (45) | 1000 | 0 | 9 | 8 | 9 |
| (53) | 1000 | 0 | 8 | 9 | 9 |
| (73) | 1000 | 0 | 10 | 10 | 10 |
| (75) | 1000 | 0 | 7 | 7 | 10 |
| (81) | 1000 | 0 | 9 | 7 | 8 |
| (83) | 1000 | 0 | 10 | 8 | 8 |

TEST EXAMPLE 9

Foliar Treatment Test in Upland Field

Vats of 33×23 cm² in area and 11 cm in depth were filled with upland field soil, and seeds of test plants shown in Table 12 were sowed in the respective vats and cultivated for 16 days. Thereafter, the test compounds were formulated into emulsifiable concentrates according to Formulation Example 2, and the prescribed amount of each emulsifiable concentrate was diluted with water at a spray volume of 1000 liters/hectare and uniformly applied from above onto the whole foliar portion of the test plants by means of a sprayer. The conditions of growth of the weed and crops at that time varied depending upon the kind of the test plants, but the test plants were in the 1- to 4-leaf stage and were 2 to 12 cm in height. Eighteen days after application, the herbicidal activity and phytotoxicity were examined. The results are shown in Table 12. This test was

TABLE 10

| Test compound | Dosage rate of active ingredient (g/ha) | Phytotoxicity | | | Herbicidal activity | | |
|---|---|---|---|---|---|---|---|
| | | Soybean | Corn | Cotton | Giant foxtail | Barnyard-grass | Johnson grass |
| (1) | 500 | 0 | 0 | 1 | 9 | 9 | 7 |
| (2) | 1000 | 2 | — | 2 | 9 | 9 | 8 |
| (11) | 1000 | 3 | 1 | 0 | 9 | 7 | 7 |
| (28) | 1000 | 0 | 0 | 0 | 9 | 8 | 8 |
| (34) | 500 | 0 | 0 | 1 | 10 | 10 | 9 |
| (70) | 250 | 1 | 0 | 2 | 8 | 7 | 10 |
| (72) | 250 | 1 | 0 | 2 | 9 | 8 | 8 |
| (82) | 1000 | 0 | 0 | 1 | 8 | 8 | 7 |
| (86) | 500 | 1 | 1 | 2 | 7 | 7 | 9 |
| (87) | 1000 | 3 | 1 | 3 | 7 | 7 | 10 |
| (90) | 1000 | 3 | 2 | 3 | 7 | 8 | 9 |
| (109) | 500 | 0 | 0 | 0 | 7 | 8 | 8 |
| (C) | 1000 | 7 | 0 | 5 | 3 | 3 | 5 | carried out in a greenhouse through the whole test period.

TABLE 12

| Test compound | Dosage rate of active ingredient (g/ha) | Phytotoxicity Corn | Herbicidal activity Morning-glory | Velvet leaf | Black nightshade |
|---|---|---|---|---|---|
| (1) | 125 | 2 | 7 | 10 | — |
| (2) | 2000 | 2 | 8 | 8 | 8 |
| (10) | 500 | 0 | 8 | 7 | 8 |
| (28) | 500 | 1 | 7 | 8 | 7 |
| (33) | 500 | 2 | 8 | 8 | 7 |
| (35) | 500 | 0 | 8 | 8 | 8 |
| (37) | 500 | 2 | 7 | 7 | 7 |
| (49) | 2000 | 3 | 9 | 8 | 7 |
| (52) | 500 | 1 | 8 | 8 | 7 |
| (65) | 500 | 1 | 7 | 7 | 7 |
| (70) | 500 | 0 | 8 | 7 | 8 |
| (108) | 500 | 2 | 7 | 8 | 8 |
| (D) | 8000 | 7 | 0 | 2 | 5 |

TEST EXAMPLE 10

Flooding Treatment Test in Paddy Field

Wager's pots of 1/5000 ares were filled with paddy field soil, and seeds of test plants shown in Table 13 were sowed. After creating a state of paddy field by water flooding, rice (at the 2-leaf stage) was transplanted and they were cultivated in a greenhouse. After 5 days (at the germination stage of barnyardgrass), the test compounds were formulated into emulsifiable concentrates according to Formulation Example 2, perscribed amount of each of the emulsifiable concentrates was diluted with water and applied onto the water surface in the pots. Water leakage decreasing the depth of flooding water by 3 cm was carried out on the day subsequent to and two days after the application of test compounds. The test plants were cultivated for 20 days in a greenhouse. Then, the herbicidal activity and phytotoxicity were examined. The results are shown in Table 13.

TABLE 13

| Test compound | Dosage rate of active ingredient (g/ha) | Phytotoxicity Rice | Herbicidal activity E. oryzicola | Ammannia multiflora | Monochoria vaginalis |
|---|---|---|---|---|---|
| (1) | 250 | 0 | 9 | 9 | 10 |
| (2) | 250 | 0 | 8 | 9 | 9 |
| (5) | 250 | 0 | 8 | 8 | 9 |
| (6) | 250 | 0 | 9 | 9 | 10 |
| (7) | 250 | 0 | 7 | 7 | 10 |
| (10) | 250 | 0 | 9 | 8 | 10 |
| (11) | 250 | 0 | 9 | 9 | 8 |
| (13) | 250 | 0 | 9 | 9 | 9 |
| (15) | 250 | 0 | 8 | 8 | 10 |
| (16) | 250 | 0 | 8 | 8 | 9 |
| (21) | 250 | 0 | 7 | 8 | 9 |
| (27) | 250 | 0 | 8 | 7 | 10 |
| (28) | 63 | 1 | 10 | 9 | 10 |
| (29) | 63 | 0 | 9 | 8 | 10 |
| (31) | 63 | 2 | 9 | 9 | 9 |
| (32) | 250 | 0 | 8 | 8 | 10 |
| (33) | 16 | 0 | 9 | 9 | 9 |
| (34) | 63 | 0 | 10 | 8 | 10 |
| (35) | 63 | 0 | 10 | 8 | 10 |
| (36) | 250 | 0 | 9 | 8 | 10 |
| (37) | 63 | 0 | 10 | 9 | 9 |
| (39) | 63 | 0 | 8 | 9 | 10 |
| (40) | 63 | 0 | 10 | 8 | 10 |
| (41) | 63 | 0 | 9 | 8 | 10 |
| (42) | 63 | 0 | 10 | 9 | 10 |
| (43) | 63 | 0 | 10 | 8 | 10 |
| (44) | 16 | 0 | 8 | 8 | 10 |
| (45) | 63 | 0 | 10 | 8 | 10 |
| (46) | 63 | 0 | 9 | 8 | 9 |
| (47) | 63 | 0 | 8 | 8 | 10 |
| (49) | 63 | 0 | 10 | 7 | 9 |
| (50) | 63 | 0 | 9 | 8 | 10 |
| (51) | 63 | 0 | 9 | 8 | 10 |
| (52) | 250 | 0 | 10 | 8 | 10 |
| (53) | 250 | 1 | 9 | 9 | 10 |
| (54) | 250 | 0 | 7 | 9 | 10 |
| (55) | 250 | 0 | 7 | 8 | 10 |
| (56) | 1000 | 0 | 8 | 8 | 10 |
| (57) | 1000 | 0 | 8 | 8 | 10 |
| (58) | 250 | 0 | 8 | 8 | 10 |
| (59) | 250 | 0 | 7 | 8 | 10 |
| (60) | 250 | 0 | 10 | 9 | 7 |
| (61) | 250 | 0 | 10 | 9 | 10 |
| (62) | 1000 | 0 | 9 | 9 | 10 |
| (65) | 63 | 0 | 8 | 9 | 8 |
| (66) | 1000 | 3 | 9 | 9 | 10 |
| (73) | 250 | 3 | 8 | 9 | 10 |
| (76) | 250 | 3 | 10 | 8 | 9 |
| (77) | 250 | 0 | 9 | 8 | 10 |
| (78) | 63 | 0 | 10 | 7 | 10 |
| (79) | 250 | 0 | 7 | 8 | 10 |
| (80) | 250 | 0 | 10 | 8 | 9 |
| (81) | 63 | 0 | 8 | 7 | 10 |
| (82) | 250 | 0 | 10 | 9 | 10 |
| (83) | 63 | 0 | 9 | 8 | 10 |
| (84) | 63 | 0 | 10 | 7 | 10 |
| (86) | 63 | 2 | 8 | 8 | 10 |
| (87) | 250 | 0 | 7 | 8 | 9 |
| (88) | 250 | 0 | 10 | 9 | 10 |
| (91) | 250 | 2 | 10 | 9 | 9 |
| (92) | 250 | 0 | 8 | 9 | 9 |
| (98) | 250 | 0 | 9 | 9 | 9 |
| (99) | 250 | 0 | 9 | 9 | 9 |
| (100) | 250 | 0 | 10 | 8 | 7 |
| (101) | 250 | 0 | 8 | 9 | — |
| (106) | 63 | 1 | 8 | 9 | 9 |
| (107) | 250 | 0 | 10 | 9 | 9 |
| (108) | 63 | 0 | 9 | 8 | 9 |
| (109) | 250 | 0 | 10 | 9 | 10 |
| (110) | 250 | 0 | 10 | 9 | 10 |
| (111) | 1000 | 1 | 9 | 8 | 10 |
| (112) | 250 | 0 | 9 | 9 | 10 |

TEST EXAMPLE 11

Flooding Treatment Test in Paddy Field

Wager's pots of 1/5000 ares were filled with paddy field soil, and seeds of test plants shown in Table 14 were sowed. After creating a state of paddy field by water flooding, rice (at the 2-leaf stage) was transplanted and they were cultivated in a greenhouse. After 12 days (at 1.5–2.0 leaves stage of barnyardgrass), the test compounds were formulated into emulsifiable concentrates according to Formulation Example 2, prescribed amount of each of the emulsifiable concentrates was diluted with water and applied onto the water surface in the pots. Water leakage decreasing the depth of flooding water by 3 cm was carried out on the day subsequent to and two days after the application of test compounds. The test plants were cultivated for 20 days in a greenhouse. Then, the herbicidal activity and phytotoxicity were examined. The results are shown in Table 14.

TABLE 14

| Test compound | Dosage rate of active ingredient (g/ha) | Phyto-toxicity Rice | Herbicidal activity E. oryzicola | Ammannia multiflora | Monochoria vaginalis |
|---|---|---|---|---|---|
| (31) | 250 | 2 | 10 | 9 | 9 |
| (33) | 63 | 0 | 8 | 8 | 10 |
| (34) | 250 | 0 | 9 | 9 | 9 |
| (35) | 63 | 0 | 9 | 8 | 9 |
| (37) | 63 | 0 | 9 | 9 | 10 |
| (41) | 63 | 0 | 9 | 8 | 10 |
| (44) | 250 | 0 | 9 | 8 | 10 |
| (45) | 63 | 0 | 9 | 8 | 10 |
| (46) | 250 | 0 | 10 | 8 | 10 |
| (49) | 63 | 0 | 10 | 8 | 10 |
| (50) | 250 | 0 | 9 | 8 | 10 |
| (51) | 250 | 0 | 9 | 9 | 10 |
| (53) | 63 | 0 | 8 | 7 | 10 |
| (61) | 250 | 0 | 10 | 8 | 10 |
| (65) | 250 | 0 | 9 | 9 | — |
| (76) | 63 | 0 | 8 | 9 | 10 |
| (78) | 63 | 0 | 10 | 8 | 10 |
| (79) | 250 | 0 | 8 | 7 | 10 |
| (80) | 250 | 2 | 9 | 8 | 10 |
| (81) | 250 | 1 | 10 | 8 | 10 |
| (82) | 250 | 0 | 9 | 8 | 10 |
| (83) | 63 | 0 | 9 | 8 | 10 |
| (84) | 63 | 0 | 9 | 8 | 9 |
| (86) | 250 | 0 | 9 | 9 | 10 |
| (88) | 250 | 0 | 9 | 9 | 10 |
| (91) | 250 | 0 | 8 | 9 | 7 |
| (100) | 250 | 0 | 7 | 9 | 8 |
| (107) | 250 | 0 | 9 | 9 | 10 |
| (108) | 250 | 1 | 9 | 9 | 9 |
| (109) | 250 | 0 | 9 | 8 | 10 |
| (110) | 250 | 0 | 9 | 8 | 10 |
| (112) | 250 | 0 | 10 | 9 | 10 |

What is claimed is:

1. A compound represented by the formula (I),

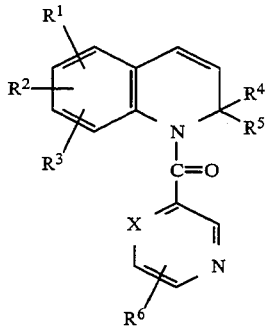

wherein each of $R^1$, $R^2$ and $R^3$, which may be the same or different, represents a hydrogen atom; a halogen atom; a $C_1$-$C_6$ alkyl group; a $C_1$-$C_6$ alkoxy group; a halo-$C_1$-$C_6$ alkyl group; a halo-$C_1$-$C_6$ alkoxy group; a ($C_1$-$C_6$ alkoxy)carbonyl group; a $C_1$-$C_6$ alkylthio group; a $C_1$-$C_6$ alkylamino group; a di($C_1$-$C_6$ alkyl)amino group; a phenyl group; or a phenoxy group, each of $R^4$ and $R^5$, which may be the same or different, represents a hydrogen atom or a $C_1$-$C_6$ alkyl group, or $R^4$ and $R^5$ are bonded together at their ends to form a $C_2$-$C_5$ alkylene group, $R^6$ represents a hydrogen atom; a halogen atom; an amino group; a $C_1$-$C_6$ alkylamino group; a di($C_1$-$C_6$ alkyl)amino group; a ($C_1$-$C_6$ alkoxy)carbonylamino group; a cyano group; or a group represented by the formula, —C(=O)—Y—$R^7$ (wherein Y represents an oxygen atom or a sulfur atom and $R^7$ represents a hydrogen atom; a $C_1$-$C_{10}$ alkyl group; a $C_2$-$C_{10}$ alkenyl group; a $C_2$-$C_{10}$ alkynyl group; a halo-$C_1$-$C_{10}$ alkyl group; a halo-$C_2$-$C_{10}$ alkenyl group; a halo-$C_2$-$C_{10}$ alkynyl group; a $C_3$-$C_{10}$ cycloalkyl group; a $C_3$-$C_{10}$ cycloalkenyl group; a $C_1$-$C_{10}$ alkoxy-$C_1$-$C_{10}$ alkyl group; a $C_1$-$C_{10}$ alkylamino-$C_1$-$C_{10}$ alkyl group; a di($C_1$-$C_{10}$ alkyl)amino-$C_1$-$C_{10}$ alkyl group; a furyl-$C_1$-$C_{10}$ alkyl group; a thienyl-$C_1$-$C_{10}$ alkyl group; a $C_1$-$C_{10}$ alkylamino group; a di($C_1$-$C_{10}$ alkyl)amino group;

—N=CH($C_1$-$C_{10}$ alkyl) group;

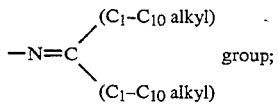

or a phenyl group optionally substituted with at least one member selected from the group consisting of ($C_1$-$C_6$ alkoxy)carbonyl groups, halogen atoms and $C_1$-$C_6$ alkyl groups; or a phenyl-$C_1$-$C_6$ alkyl group optionally substituted with at least one member selected from the group consisting of ($C_1$-$C_6$ alkoxy)carbonyl groups, halogen atoms and $C_1$-$C_6$ alkyl groups); or a group represented by the formula,

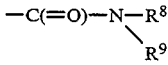

(wherein each of $R^8$ and $R^9$, which may be the same or different, represents a hydrogen atom; a $C_1$-$C_6$ alkyl group; a $C_2$-$C_6$ alkenyl group; a $C_2$-$C_6$ alkynyl group; a halo-$C_1$-$C_6$ alkyl group; a halo-$C_2$-$C_6$ alkenyl group; a halo-$C_2$-$C_6$ alkynyl group; a $C_3$-$C_6$ cycloalkyl group; a $C_3$-$C_6$ cycloalkenyl group; an amino group; a $C_1$-$C_6$ alkylamino group; a di($C_1$-$C_6$ alkyl)amino group; or a phenyl group optionally substituted with at least one member selected from the group consisting of halogen atoms and $C_1$-$C_6$ alkyl groups; or a phenyl-$C_1$-$C_6$ alkyl group optionally substituted with at least one member selected from the group consisting of halogen atoms and $C_1$-$C_6$ alkyl groups), X represents CH or a nitrogen atom.

2. A compound according to claim 1, wherein each of $R^1$, $R^2$ and $R^3$, which may be the same or different, represents a hydrogen atom; a halogen atom; a $C_1$-$C_3$ alkyl group; a $C_1$-$C_3$ alkoxy group; a halo-$C_1$-$C_3$ alkyl group; a halo-$C_1$-$C_3$ alkoxy group; a ($C_1$-$C_3$ alkoxy)carbonyl group; a $C_1$-$C_3$ alkylthio group; a $C_1$-$C_3$ alkylamino group; a di($C_1$-$C_3$ alkyl)amino group; a phenyl group; or a phenoxy group, each of $R^4$ and $R^5$, which may be the same or different, represents a hydrogen atom or a $C_1$-$C_3$ alkyl group, or $R^4$ and $R^5$ are bonded together at their ends to form a $C_2$-$C_3$ alkylene group, $R^6$ represents a hydrogen atom; a halogen atom; an amino group; a $C_1$-$C_3$ alkylamino group; a di($C_1$-$C_3$ alkyl)amino group; a ($C_1$-$C_3$ alkoxy)carbonylamino group; a cyano group; or a group represented by the formula, —C(=O)—Y—$R^7$ (wherein Y represents an oxygen atom or a sulfur atom and $R^7$ represents a hydrogen atom; a $C_1$-$C_6$ alkyl group; a $C_2$–$C_6$ alkenyl group; a $C_2$–$C_6$ alkynyl group; a halo-$C_1$–$C_6$ alkyl group; a halo-$C_2$–$C_6$ alkenyl group; a halo-$C_2$–$C_6$ alkynyl group; a $C_3$–$C_6$ cycloalkyl group; a $C_3$–$C_6$ cycloalkenyl group; a $C_1$–$C_6$ alkoxy-$C_1$–$C_6$ alkyl group; a $C_1$–$C_6$ alkylamino-$C_1$–$C_6$ alkyl group; a di($C_1$–$C_6$ alkyl)amino-$C_1$–$C_6$ alkyl group; a furyl-$C_1$–$C_6$ alkyl group; a thienyl-$C_1$–$C_6$ alkyl group; a $C_1$–$C_6$ alkylamino group; a di($C_1$–$C_6$ alkyl)amino group;

—N=CH($C_1$–$C_6$ alkyl) group;

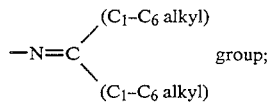 group;

or a phenyl group optionally substituted with at least one member selected from the group consisting of ($C_1$–$C_6$ alkoxy)carbonyl groups, halogen atoms and $C_1$–$C_6$ alkyl groups; or a phenyl-$C_1$–$C_6$ alkyl group optionally substituted with at least one member selected from the group consisting of ( $C_1$–$C_6$ alkoxy) carbonyl groups, halogen atoms and $C_1$–$C_6$ alkyl groups); or a group represented by the formula,

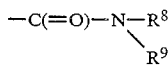

(wherein each of $R^8$ and $R^9$, which may be the same or different, represents a hydrogen atom; a $C_1$–$C_6$ alkyl group; a $C_2$–$C_6$ alkenyl group; a $C_2$–$C_6$ alkynyl group; a halo-$C_1$–$C_6$ alkyl group; a halo-$C_2$–$C_6$ alkenyl group; a halo-$C_2$–$C_6$ alkynyl group; a $C_3$–$C_6$ cycloalkyl group; a $C_3$–$C_6$ cycloalkenyl group; an amino group; a $C_1$–$C_6$ alkylamino group; a di($C_1$–$C_6$ alkyl)amino group; or a phenyl group optionally substituted with at least one member selected from the group consisting of halogen atoms and $C_1$–$C_6$ alkyl groups; or a phenyl-$C_1$–$C_6$ alkyl group optionally substituted with at least one member selected from the group consisting of halogen atoms and $C_1$–$C_6$ alkyl groups), X represents CH or a nitrogen atom.

3. A compound according to claim 1, wherein each of $R^4$ and $R^5$, which may be the same or different, represents a $C_1$–$C_3$ alkyl group.

4. A compound according to claim 1, wherein $R^4$ and $R^5$ represent methyl groups.

5. A compound according to claim 1, wherein

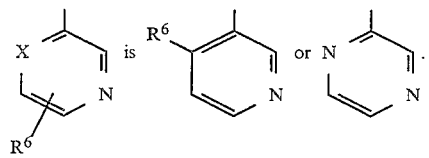

6. A compound according to claim 2, wherein $R^6$ represents a hydrogen atom; a halogen atom; a cyano group; a group represented by the formula, —C(=O)—Y—$R^7$; or a group represented by the formula,

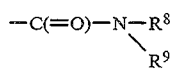

(wherein $R^7$, $R^8$, $R^9$ and Y are as defined in claim 2).

7. A compound according to claim 6, wherein $R^6$ represents a group represented by the formula, —C(=O)—Y—$R^7$; or a group represented by the formula,

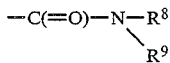

(wherein $R^7$, $R^8$, $R^9$ and Y are as defined in claim 2).

8. A compound according to claim 1, wherein $R^1$ is at 6-position and $R^2$ and $R^3$ represent hydrogen atoms.

9. A compound according to claim 8, wherein $R^1$ is a halogen atom; a $C_1$–$C_3$ alkyl group; or a phenyl group.

10. A compound according to claim 9 wherein $R^1$ is a halogen atom.

11. A herbicidal composition which comprises as an active ingredient a herbicidally effective amount of the compound (I) according to claim 1 and an inert carrier or a diluent.

12. A method for controlling undesired weeds, which comprises applying a herbicidally effective amount of the compound (I) according to claim 1 to the area where undesired weeds grow or will grow.

* * * * *